US010068173B2

(12) United States Patent
Vayser et al.

(10) Patent No.: US 10,068,173 B2
(45) Date of Patent: Sep. 4, 2018

(54) MEDICAL DEVICE FEATURING CLADDED WAVEGUIDE

(71) Applicant: Invuity, Inc., San Francisco, CA (US)

(72) Inventors: Alex Vayser, Mission Viejo, CA (US); Fernando Erismann, New York, NY (US); Gaston Tudury, San Francisco, CA (US)

(73) Assignee: INVUITY, INC., San Francisco, CA (US)

( * ) Notice: Subject to any disclaimer, the term of this patent is extended or adjusted under 35 U.S.C. 154(b) by 0 days.

(21) Appl. No.: 14/719,201

(22) Filed: May 21, 2015

(65) Prior Publication Data

US 2016/0015467 A1    Jan. 21, 2016

Related U.S. Application Data

(60) Provisional application No. 62/002,030, filed on May 22, 2014.

(51) Int. Cl.
*A61B 1/32* (2006.01)
*G06N 5/02* (2006.01)
(Continued)

(52) U.S. Cl.
CPC ............... *G06N 5/02* (2013.01); *A61B 1/07* (2013.01); *A61B 17/02* (2013.01); *G02B 1/048* (2013.01); *G02B 6/0001* (2013.01); *G09B 5/06* (2013.01); *G09B 19/003* (2013.01); *A61B 1/0017* (2013.01); *A61B 2017/3445* (2013.01); *A61B 2217/005* (2013.01)

(58) Field of Classification Search
CPC ....... A61B 1/06; A61B 1/0607; A61B 1/0615; A61B 1/0623; A61B 1/063; A61B 1/0638; A61B 1/0646; A61B 1/0653; A61B 1/0661; A61B 1/0669; A61B 1/0676; A61B 1/0684; A61B 1/0692; A61B 1/07; A61B 1/00163; A61B 1/00165; A61B 1/00167; A61B 1/0017
USPC ................ 600/200, 223, 241, 245, 248, 249
See application file for complete search history.

(56) References Cited

U.S. PATENT DOCUMENTS 4,562,832 A * 1/1986 Wilder ..................... A61B 1/32
                                                        138/DIG. 8
5,213,092 A * 5/1993 Uram .................. A61B 1/00165
                                                        600/156
(Continued)

FOREIGN PATENT DOCUMENTS

WO    WO-2009116969 A1    9/2009

OTHER PUBLICATIONS

International search report and written opinion dated Oct. 26, 2015 for PCT/US2015/032072.

(Continued)

*Primary Examiner* — Eduardo C Robert
*Assistant Examiner* — Michelle C. Eckman
(74) *Attorney, Agent, or Firm* — Wilson Sonsini Goodrich & Rosati; Jonathan Feuchtwang

(57) ABSTRACT

Various surgical devices having integrated means of illuminating a surgical field are provided. Retractors, cannulas, suction devices and the like are disclosed having integrated optical waveguides coupleable to external lighting sources. The waveguides feature cladding layers configured to enhance transmission efficiency.

31 Claims, 28 Drawing Sheets

(51) Int. Cl.
*G09B 5/06* (2006.01)
*G09B 19/00* (2006.01)
*A61B 17/02* (2006.01)
*G02B 1/04* (2006.01)
*F21V 8/00* (2006.01)
*A61B 1/07* (2006.01)
*A61B 17/34* (2006.01)
*A61B 1/00* (2006.01)

(56) References Cited

U.S. PATENT DOCUMENTS

| | | | |
|---|---|---|---|
| 5,248,311 A | 9/1993 | Black et al. | |
| 5,898,810 A * | 4/1999 | Devens, Jr. | B29C 47/0023 385/123 |
| 6,343,174 B1 | 1/2002 | Neuberger | |
| 7,223,233 B2 * | 5/2007 | Branch | A61B 17/0218 600/212 |
| 7,469,082 B1 * | 12/2008 | Okorogu | G02B 6/34 385/15 |
| 7,874,982 B2 * | 1/2011 | Selover | A61B 17/02 600/199 |
| 7,901,353 B2 | 3/2011 | Vayser et al. | |
| 7,991,257 B1 * | 8/2011 | Coleman | B29D 11/0073 264/1.24 |
| 8,088,066 B2 | 1/2012 | Grey et al. | |
| 8,162,824 B2 | 4/2012 | Vayser et al. | |
| 8,292,805 B2 | 10/2012 | Vayser et al. | |
| 8,409,088 B2 | 4/2013 | Grey et al. | |
| 8,948,560 B1 * | 2/2015 | Wach | G02B 6/032 385/115 |
| 2002/0172478 A1 * | 11/2002 | Sahlin | G02B 6/4429 385/104 |
| 2004/0143169 A1 * | 7/2004 | Branch | A61B 90/36 600/245 |
| 2005/0171408 A1 * | 8/2005 | Parker | A61B 90/35 600/249 |
| 2005/0279354 A1 * | 12/2005 | Deutsch | A61B 1/07 128/200.24 |
| 2006/0099426 A1 * | 5/2006 | Bekiarian | C08F 222/18 428/421 |
| 2006/0211918 A1 * | 9/2006 | Lieponis | A61M 1/008 600/182 |
| 2006/0217596 A1 * | 9/2006 | Williams | A61B 17/02 600/245 |
| 2006/0224045 A1 * | 10/2006 | Whipple | A61B 17/3421 600/245 |
| 2006/0268570 A1 * | 11/2006 | Vayser | A61B 1/00135 362/572 |
| 2007/0167682 A1 * | 7/2007 | Goldfarb | A61B 1/00135 600/114 |
| 2007/0208226 A1 * | 9/2007 | Grey | A61B 17/02 600/212 |
| 2007/0239149 A1 * | 10/2007 | Lieponis | A61B 1/00165 606/15 |
| 2008/0002426 A1 * | 1/2008 | Vayser | A61B 1/0623 362/574 |
| 2008/0108877 A1 * | 5/2008 | Bayat | A61B 17/02 600/214 |
| 2008/0255545 A1 * | 10/2008 | Mansfield | A61F 9/007 606/4 |
| 2008/0275325 A1 * | 11/2008 | Miyakawa | A61B 5/0071 600/368 |
| 2009/0022456 A1 * | 1/2009 | Schmadel | B82Y 20/00 385/43 |
| 2009/0036744 A1 * | 2/2009 | Vayser | A61B 1/00096 600/182 |
| 2009/0105546 A1 * | 4/2009 | Hestad | A61B 17/0206 600/210 |
| 2009/0112068 A1 * | 4/2009 | Grey | A61B 17/02 600/212 |
| 2009/0221991 A1 * | 9/2009 | Lieponis | A61B 1/00105 604/540 |
| 2009/0269016 A1 * | 10/2009 | Korampally | C01B 33/12 385/129 |
| 2010/0021114 A1 * | 1/2010 | Chen | G02B 6/02214 385/116 |
| 2010/0041955 A1 * | 2/2010 | Grey | A61B 1/267 600/212 |
| 2010/0274097 A1 * | 10/2010 | Cho | A61B 17/0206 600/249 |
| 2011/0069969 A1 * | 3/2011 | Hochberg | B82Y 20/00 398/141 |
| 2011/0112376 A1 * | 5/2011 | Vayser | A61B 1/0017 600/249 |
| 2012/0041268 A1 * | 2/2012 | Grey | A61B 1/00105 600/199 |
| 2012/0212595 A1 * | 8/2012 | Parmar | A61B 5/0062 348/68 |
| 2013/0012783 A1 * | 1/2013 | Vayser | A61B 1/00135 600/249 |
| 2013/0064515 A1 * | 3/2013 | Shurgalin | A61B 18/22 385/125 |
| 2013/0155723 A1 | 6/2013 | Coleman et al. | |
| 2013/0156392 A1 * | 6/2013 | Logunov | G02B 6/0003 385/123 |
| 2013/0197313 A1 * | 8/2013 | Wan | A61B 1/32 600/202 |
| 2013/0267786 A1 * | 10/2013 | Vayser | A61B 1/32 600/205 |
| 2013/0317312 A1 | 11/2013 | Eastlack et al. | |
| 2013/0322092 A1 * | 12/2013 | Eisenkolb | A61B 1/00096 362/322 |
| 2014/0088371 A1 * | 3/2014 | Vayser | A61B 1/00135 600/249 |
| 2014/0121469 A1 * | 5/2014 | Meckel | A61F 9/00821 600/249 |
| 2014/0133173 A1 * | 5/2014 | Vayser | A61B 17/0206 362/572 |
| 2014/0221763 A1 * | 8/2014 | Vayser | A61B 19/5202 600/245 |
| 2014/0296805 A1 * | 10/2014 | Arthur | A61M 1/0049 604/319 |
| 2014/0355295 A1 * | 12/2014 | Kuchinisky | G02B 6/001 362/558 |
| 2015/0011837 A1 * | 1/2015 | Johnson | G02B 6/443 600/249 |
| 2015/0080666 A1 * | 3/2015 | Vayser | A61M 1/008 600/245 |
| 2015/0376302 A1 * | 12/2015 | Abe | C08F 8/22 525/356 |
| 2016/0015467 A1 * | 1/2016 | Vayser | G06N 5/02 600/245 |
| 2016/0246004 A1 * | 8/2016 | Kachru | G02B 6/26 |

OTHER PUBLICATIONS

European search report with written opinion dated Jan. 12, 2018 for EP Application No. 15796871.

* cited by examiner

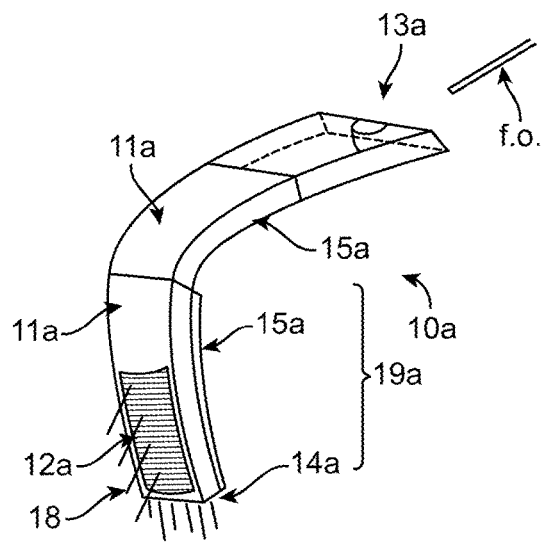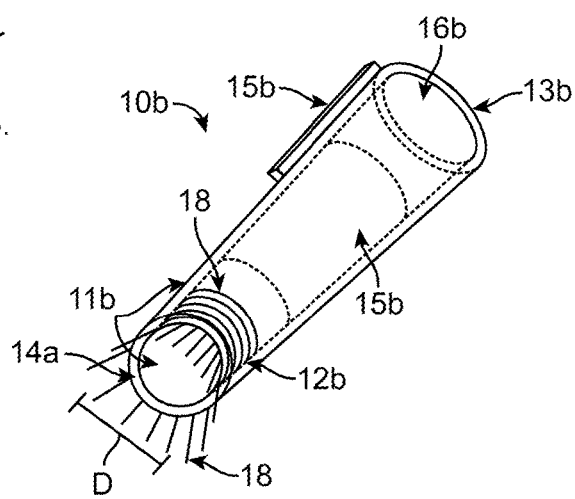
FIG. 1A    FIG. 1B
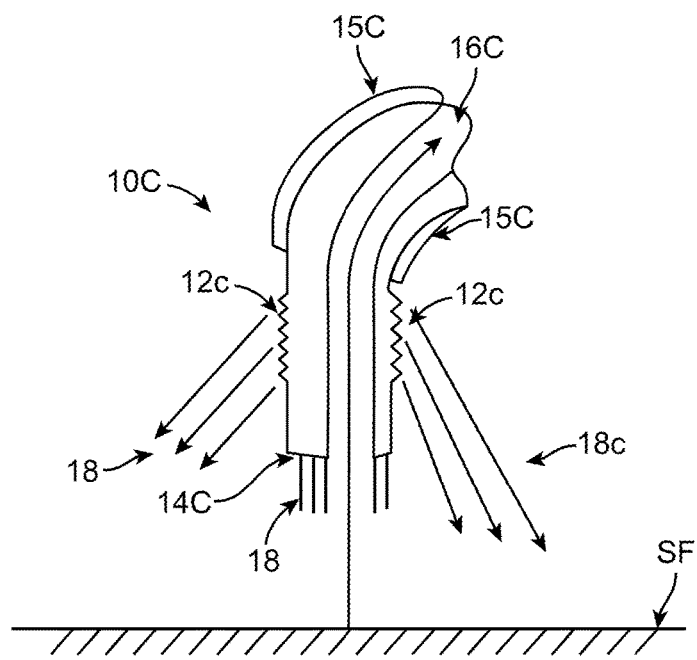
FIG. 1C

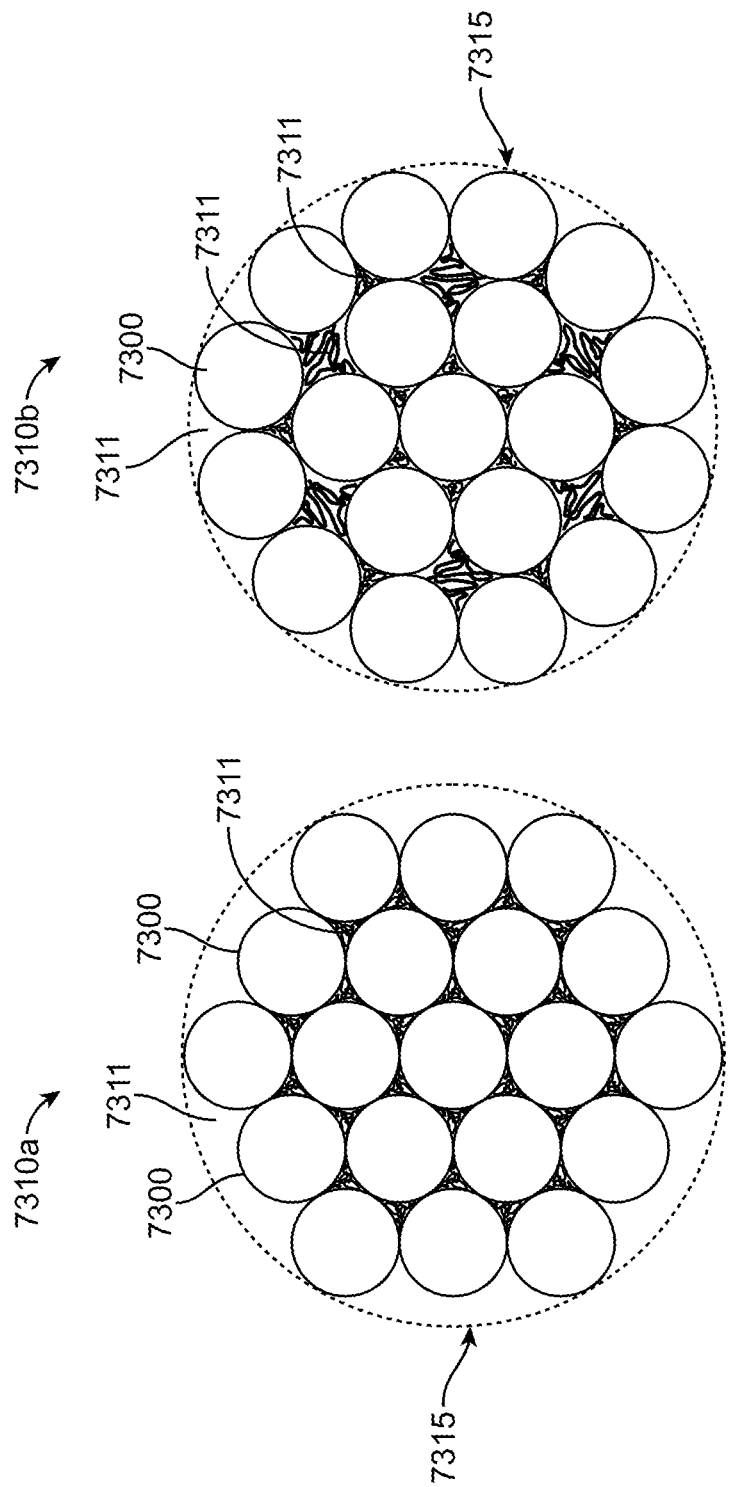

MEDICAL DEVICE FEATURING CLADDED WAVEGUIDE

CROSS-REFERENCE

The present application is a non-provisional of, and claims the benefit of U.S. Provisional Patent Application No. 62/002,030 filed May 22, 2014; the entire contents of which are incorporated herein by reference.

This application is related to the following U.S. patent application Ser. No. 14/068,695 filed Oct. 31, 2013; Ser. No. 12/188,055 filed Aug. 7, 2008; Ser. No. 14/063,910 filed Oct. 25, 2013; Ser. No. 14/068,571 filed Oct. 31, 2013; Ser. No. 14/057,933 filed Oct. 18, 2013; Ser. No. 13/026,910 filed Feb. 14, 2011; Ser. No. 13/712,029 filed Dec. 12, 2012; the entire contents of which are incorporated herein by reference.

BACKGROUND OF THE INVENTION

1. Field of the Invention

The inventions described below relate generally to medical systems, medical devices and methods and more specifically relate to illumination of a work area such as a surgical field.

2. Background of the Invention

Illumination of body cavities or surgical fields for diagnosis and/or therapy has been limited by overhead illumination. High intensity incandescent lighting has been developed and has received limited acceptance along with semiconductor and laser lighting. These light sources have a heat and weight penalty associated with their use. Additionally, such lighting sources can be cumbersome due to creation of shadows in the illuminated body cavity or surgical field. Excessive heat can cause unwanted coagulation of blood, as well as unnecessary heating of a patient's body. Additionally, heat buildup can cause various components fabricated from some polymers to exceed their glass transition temperature and deform. Heat buildup may also cause optical properties of various components to be compromised. Some of these systems are heavy and the weight of these illumination systems makes them uncomfortable for an operator, especially during a lengthy procedure. Conventional light sources rely on fiber optic and similar waveguide materials to conduct light to a body cavity or surgical field. These conventional sources and materials often suffer from poor light transmission and conduction inefficiencies, which may exacerbate excessive heating problems and result in weak illumination of the body cavity or surgical field.

Examples of conventional waveguide polymers that have traditionally been used with some success in surgical illumination systems include acrylics such as polymethylmethacrylate (PMMA) and polycarbonates (PC) such as Lexan®. Effective illumination during surgery requires efficiently conducting light through these waveguide materials. During typical use waveguides constructed from these materials come into contact with various materials such as blood, water, fat, skin, and hardware from adjacent medical devices. Contact between the waveguide and these various materials (environmental media) can induce light transmission losses via frustrated total internal reflection (TIR). Light losses via frustrated TIR may also occur when such waveguides are attached/glued to other devices for mechanical or therapeutic reasons. Normally these materials conduct light via TIR, wherein light traveling within the material is completely reflected at a boundary interface of the material when the light strikes that boundary interface at an angle equal to or below a critical angle. During TIR a portion of electric and magnetic (E/M) fields that make up light will extend a short distance past the material's boundary interface (into the external environment) this happens because electromagnetic fields must be continuous. This portion of the E/M field that extends past the waveguide's reflective boundary is known as an evanescent wave. If the evanescent wave finds an absorptive media, or a media with a higher index of refraction, within a few wavelengths of the boundary, then the evanescent wave may couple into environmental media. This causes frustrated TIR wherein light that would normally be contained within the waveguide material leaks out despite TIR conditions being met. Frustrated TIR is more likely to happen for light striking the waveguide material's boundary interface at an angle close to the critical angle for TIR. Frustrated TIR causes significant losses in light conduction and transmission efficiency and exacerbates extraneous heating of the waveguide materials and surrounding tissues, and degrades the quality of illumination provided to the body cavity or surgical field. Applying reflective coatings in attempt to prevent light from leaking out of the waveguide can present problems as well. Absorptive losses within reflective coating materials can generate unwanted amounts of heat and reduce the optical transmission efficiency of the waveguide. Therefore, it would be advantageous to provide improved illumination systems having waveguides and materials that minimize light losses from frustrated TIR. At least some of these objectives will be met by the exemplary embodiments described below.

SUMMARY OF THE INVENTION

Aspects of the present disclosure provide a system for illuminating a surgical field comprising a surgical instrument, and a non-fiber optical waveguide engaged with at least a portion of the surgical instrument. The optical waveguide is typically configured to conduct light to the surgical field. The optical waveguide also typically comprises an optical cladding (also referred to as cladding or cladding layer or optical cladding layer) that is disposed upon at least a portion of the optical waveguide. The optical cladding is typically disposed about an exterior surface of the waveguide. The optical cladding typically has a thickness of at least 350 nm to thereby prevent evanescent waves of conducted light from coupling to the environment surrounding the waveguide. Such environment may include but is not limited to tissue, blood, other bodily fluids, or other adjacent medical devices. The cladding may thus serve to prevent the conducted light from leaking out of the waveguide until the waveguide can conduct/direct the light to the surgical field. The adjacent medical device may be a surgical instrument which may comprise but is not limited to at least one or more of the following: a retractor, a suction instrument, or a cannula.

Optionally, the optical cladding may have a refractive index greater than 1 and less than the refractive index of the optical waveguide's light conducting material.

The optical waveguide may comprise a receiving portion configured to receive light. The received light may then be conducted to the surgical field by the optical waveguide in order to illuminate the surgical field. The received light typically comes from a light source, the light source being optically coupled to the receiving portion. The light source may comprise a light emitting diode (LED), incandescent bulb, xenon flash lamp, laser, or any other light source known in the art. Optionally the light source is disposed upon or within the receiving portion of the waveguide. For example, the light source may comprise a LED that is disposed within the optical waveguide at the receiving portion, thereby allowing light emitted from the LED (or any other light source) to enter the optical waveguide at the receiving portion and to be conducted by the optical waveguide. The light source may also be disposed on or adjacent a surface of the receiving portion such that light emitted from the light source enters the optical waveguide through the surface of the receiving portion.

Optionally, the light source may be optically coupled to the receiving portion of the optical waveguide by a flexible input (also referred to as a "pigtail" or "pigtail connection"). The pigtail typically comprises a light conducting material configured to conduct light from the light source to the receiving portion of the optical waveguide. The pigtail may comprise one or more optical fibers. The pigtail may comprise a plurality of optical fibers. The plurality of optical fibers may be arranged into one or more bundles. Each bundle may comprise a fiber optic ribbon or cable. The plurality of optical fibers of each bundle may be arranged such a cross section of each bundle shows the optical fibers arranged in one or more patterns. The one or more patterns may include concentric circles, concentric hexagons, and/or rectangles. One or more of the optical fibers of the one or more bundles may comprise an optical cladding. The pigtail may comprise multiple bundles (also referred to as "cables") that are connected by optical connectors. The pigtail may be optically coupled to the receiving portion of the optical waveguide via one or more of the following: an optical connector (or adapter), an end-to-end ("butt" or "abutting") coupling between the pigtail's light conducting material and a surface of the optical waveguide's receiving portion, and/or a portion of the pigtail that protrudes into the optical waveguide.

Aspects of the present disclosure provide a system for illuminating a surgical field comprising an optical waveguide having an input, an output, and an exterior surface; the system being configured to receive light from an illumination source and to conduct the received light via total internal reflection (TIR) from the input to the output. The conducted light upon reaching the output will exit the optical waveguide to illuminate the surgical field. The optical waveguide may comprise a cyclo olefin polymer (COP) or a cyclo olefin copolymer (COCP). The optical waveguide may alternatively comprise any other suitable optical polymer. The optical waveguide may comprise one or more cladding layers (also referred to as an optical cladding layer) disposed upon at least a portion of the exterior surface. The exterior surface typically comprises a boundary surface between the waveguide material and an environment external to the waveguide (such as blood, tissue, bone, and or part of an adjacent medical device). In some embodiments the waveguide may be hollow and comprise an interior surface wherein the interior surface is the boundary surface between the waveguide material and the hollow space of the hollow waveguide. In such embodiments the internal surface may also feature one or more cladding layers. The one or more cladding layers may be configured to improve TIR by providing an optical material layer comprising a fluoropolymer such as one or more of the following materials: fluoro acrylate, a fluoro methylacrylate, or polytetrafluoroethylene (PTFE) and having a thickness greater than 350 nanometers, thereby preventing evanescent waves of the conducted light from coupling to material outside the optical waveguide. Other cladding materials may also be used. The cladding layer may comprise one or more additional material layers, which may be stacked upon one another. For instance, an adhesive layer comprising an adhesive may be stacked on top of the optical material layer to provide adhesive functionality to the cladding layer. A hydrophobic material layer may likewise be applied such that the cladding layer repels bodily fluid in addition to improving TIR. The cladding layer(s) may be applied to the waveguide in a dip coating process (or other liquid application process), heat shrink process, or vapor deposition process, or other processes known in the art. The features of the cladding layer described herein may be used in any cladding layer described throughout this application, including cladding layers applied to waveguides of any of the embodiments disclosed herein.

Aspects of the present disclosure provide a surgical retractor illumination system comprising a light source, a retractor, and a non-fiber optical waveguide. The retractor typically has a front surface, a rear surface, a distal end, a proximal end, and is shaped such that the rear surface is adapted to engage and/or distract or retract tissue to thereby expose a surgical field with the front surface of the retractor facing the surgical field. The non-fiber optical waveguide may be disposed over the front surface of the retractor and may conform to the shape of the retractor. The optical waveguide may comprise COP or COCP. Alternatively, the waveguide may comprise any other optically transparent material. In many embodiments the waveguide is removably secured to the retractor or surgical instrument to conduct light through the front and/or rear surfaces of the retractor. The optical waveguide typically comprises an input portion (also referred to as an input section or receiving portion) for receiving light from the light source and is configured to conduct the received light via TIR to one or more light emitting surfaces, where the conducted light leaves the optical waveguide and illuminates the surgical field. Such light emitting surfaces may comprise a plurality of facets and/or steps or microstructures. The optical waveguide may further comprise an exterior surface and one or more cladding layers disposed on at least a portion of the exterior surface and adapted to promote TIR by preventing evanescent wave leakage/coupling. The exterior surface typically comprises a boundary surface between the waveguide material and an environment external to the waveguide (such as blood, tissue, bone, and/or part of a medical device). In some embodiments, the waveguide may be hollow and comprise an interior surface wherein the interior surface is the boundary surface between the waveguide material and the hollow space of the hollow waveguide. In such embodiments the internal surface may also feature one or more cladding layers. In many embodiments, the one or more cladding layers may comprise one or more of the following materials: fluoro acrylate, a fluoro methylacrylate, or polytetrafluoroethylene (PTFE) and have a thickness of at least 350 nanometers. Other fluoro-polymer materials known in the art may also be used. The inventors have found that a coating thickness of 350 nanometers is sufficient to prevent frustrated TIR for an unexpected variety of waveguide geometries. The index of refraction of the coating materials disclosed herein is chosen to promote TIR. Preferably the cladding layer material has an index of refraction as close to 1.0 as possible which is the index of refraction for air.

Optionally, the optical waveguide comprises a plurality of zones for illuminating the surgical field, the plurality of facets disposed in the plurality of zones, and wherein at least some of the plurality of facets in a first zone is different than the plurality of facets in a second zone.

Optionally the optical waveguide has a cross-section with a width and a thickness, the thickness may change from a proximal end of the optical waveguide toward a distal end thereof.

The optical waveguide may comprise a receiving portion configured to receive light. The received light may then be conducted to the surgical field by the optical waveguide in order to illuminate the surgical field. The received light typically comes from a light source, the light source being optically coupled to the receiving portion. The light source may comprise a light emitting diode (LED), incandescent bulb, xenon flash lamp, laser, or any other light source known in the art. Optionally the light source is disposed upon or within the receiving portion of the waveguide. For example, the light source may comprise a LED that is disposed within the optical waveguide at the receiving portion, thereby allowing light emitted from the LED (or any other light source) to enter the optical waveguide at the receiving portion and to be conducted by the optical waveguide. The light source may also be disposed on or adjacent a surface of the receiving portion such that light emitted from the light source enters the optical waveguide through the surface of the receiving portion.

Optionally, the light source may be optically coupled to the receiving portion of the optical waveguide by a flexible input (also referred to as a "pigtail" or "pigtail connection"). The pigtail typically comprises a light conducting material configured to conduct light from the light source to the receiving portion of the optical waveguide. The pigtail may comprise one or more optical fibers. The pigtail may comprise a plurality of optical fibers. The plurality of optical fibers may be arranged into one or more bundles. Each bundle may comprise a fiber optic ribbon or cable. The plurality of optical fibers of each bundle may be arranged such that a cross section of each bundle shows the optical fibers arranged in one or more patterns. The one or more patterns may include concentric circles, concentric hexagons, and/or rectangles. One or more of the optical fibers of the one or more bundles may comprise an optical cladding. The pigtail may comprise multiple bundles (also referred to as "cables") that are connected by optical connectors. The pigtail may be optically coupled to the receiving portion of the optical waveguide via one or more of the following: an optical connector (or adapter), an end-to-end ("butt" or "abutting") coupling between the pigtail's light conducting material and a surface of the optical waveguide's receiving portion, and/or a portion of the pigtail that protrudes into the optical waveguide.

A second aspect of the disclosure provides a surgical instrument and integrated illumination system for illuminating a surgical field. Optionally the surgical instrument and integrated illumination system comprises a surgical retractor illumination system. Such a system may typically comprise a retractor blade, a non-fiber optical waveguide having an exterior surface, and one or more cladding layers disposed about the exterior surface of the optical waveguide. The optical waveguide may comprise COP or COCP. The retractor blade typically comprises a front side, a back side, and one or more engagement elements disposed on the retractor blade. The back side of the retractor blade is typically adapted to engage tissue at a surgical site. In many embodiments the optical waveguide has a front surface and a rear surface and is disposed adjacent the retractor blade such that the rear surface of the optical waveguide is disposed adjacent the front side of the retractor blade. The optical waveguide may further comprise a plurality of active zones through which light passes by TIR to one or more output zones configured to project the passing light onto the surgical field, one or more dead zones where TIR does not occur, and one or more engagement elements disposed in the one or more dead zones. Optionally, the one or more cladding layers comprise one or more of the following materials: fluoro acrylate, a fluoro methylacrylate, or polytetrafluoroethylene (PTFE), have a thickness of at least 350 nanometers, and is thereby configured to prevent evanescent waves of the passing (conducted) light from coupling to any medium adjacent the optical waveguide. Such media may include, for example, blood or other bodily fluids adjacent the surgical instrument. The one or more engagement elements of the retractor blade may releasably engage the one or more elements of the optical waveguide, such engagement may maintain an air gap between the active zones of the optical waveguide and the retractor blade. In some embodiments, the one or more engagement elements of the optical waveguide comprise regions of the cladding layer.

Optionally the optical waveguide and retractor blade may contact/abut each other. In such embodiments, the optical waveguide and the retractor blade may each comprise one or more shared surfaces where the optical waveguide and retractor blade contact/abut each other. To prevent frustrated TIR and light coupling/leaking into to the retractor blade, the exterior surface of the optical waveguide may feature/comprise the one or more cladding layers. The cladding may be disposed upon (or cover) at least a portion of the optical waveguide's shared surface(s) such that the one or more cladding layers contacts the retractor blade instead of the optical waveguide's light conducting material (e.g. COP/COCP). Optionally, the rear surface of the optical waveguide abuts the front side of the retractor blade and the optical waveguide's shared surface(s) are located on at least the rear surface of the optical waveguide. In some embodiments, the entire rear surface of the optical waveguide may comprise/feature the one or more cladding layers. Optionally a portion of the rear surface comprises/features the one or more cladding layers. Optionally, when a portion of the rear surface comprises an optical cladding, the cladding may cover at least the entirety of the rear surface's shared surface(s). For instance, if the optical waveguide's rear surface is larger than the front side of the retractor blade that abuts it, the cladding may cover a portion or an entirety of the rear surface's shared surface(s) without covering the entirety of the optical waveguide's rear surface. Optionally, the cladding is disposed about a perimeter of optical waveguide's shared surface(s). The perimeter of cladding creates a standoff that seals off an air gap between the optical waveguide and the retractor blade. The air gap may also function to prevent frustrated TIR, while the perimeter of cladding functions to keep blood or other bodily fluids from entering the air gap.

Optionally, the optical waveguide comprises a light input portion (also referred to as receiving portion) having an input dead zone where TIR does not occur, and an input collar connected to the optical waveguide in the input dead zone, the input collar surrounding the light input portion and forming an input air gap at least partially or fully circumferentially therearound. In some embodiments the light input collar may comprise a cladding layer adapted to prevent light from leaking out a circumferential side of the light input portion.

The optical waveguide may comprise a receiving portion configured to receive light. The received light may then be conducted to the surgical field by the optical waveguide in order to illuminate the surgical field. The received light typically comes from a light source, the light source being optically coupled to the receiving portion. The light source may comprise a light emitting diode (LED), incandescent bulb, xenon flash lamp, laser, combinations thereof, or any other light source known in the art. In some embodiments the light source is disposed upon or within the receiving portion of the waveguide. For example, the light source may comprise a LED that is disposed within the optical waveguide at the receiving portion, thereby allowing light emitted from the LED (or any other light source) to enter the optical waveguide at the receiving portion and to be conducted by the optical waveguide. The light source may also be disposed on or adjacent a surface of the receiving portion such that light emitted from the light source enters the optical waveguide through the surface of the receiving portion.

Optionally, the light source may be optically coupled to the receiving portion of the optical waveguide by a flexible input (also referred to as a "pigtail" or "pigtail connection"). The pigtail typically comprises a light conducting material configured to conduct light from the light source to the receiving portion of the optical waveguide. The pigtail may comprise one or more optical fibers. The pigtail may comprise a plurality of optical fibers. The plurality of optical fibers may be arranged into one or more bundles. Each bundle may comprise a fiber optic ribbon or cable. The plurality of optical fibers of each bundle may be arranged such a cross section of each bundle shows the optical fibers arranged in one or more patterns. The one or more patterns may include concentric circles, concentric hexagons, and/or rectangles. One or more of the optical fibers of the one or more bundles may comprise an optical cladding. The pigtail may comprise multiple bundles (also referred to as "cables") that are connected by optical connectors. The pigtail may be optically coupled to the receiving portion of the optical waveguide via one or more of the following: an optical connector (or adapter), an end-to-end ("butt" or "abutting") coupling between the pigtail's light conducting material and a surface of the optical waveguide's receiving portion, and/or a portion of the pigtail that protrudes into the optical waveguide.

Aspects of the disclosure provide an illuminated surgical suction device comprising a suction tube, the suction tube having a proximal and a distal end connected by a central portion, an inner surface and an outer surface. The proximal end is adapted to fluidly connect to a vacuum source. The illuminated suction device may also comprise a cladding layer on an outer surface of the central portion of the suction tube. The illuminated suction device may further comprise a non-fiber optical waveguide having an internal surface, an external surface, a cross-sectional area, a proximal end, and a distal end. The optical waveguide may comprise COP or COCP. The optical waveguide is configured to conduct light via TIR. The cladding layer may comprise one or more of the following materials: fluoro acrylate, a fluoro methylacrylate, or polytetrafluoroethylene (PTFE), have a thickness of at least 350 nanometers, and is thereby configured to prevent or minimize evanescent waves of the conducted light from coupling to a medium outside the optical waveguide. The illuminated suction device may further comprise an illumination input formed into the proximal end of the optical waveguide for receiving light from a source into the optical waveguide. Typically the optical waveguide transmits (or conducts) light received at its proximal end towards its distal end. The optical waveguide may be disposed about the cladding layer on the central portion of the suction tube such that the cladding layer is disposed between the suction tube and the internal surface of the optical waveguide to thereby prevent or minimize evanescent waves of the conducted light from coupling to the suction tube. In addition to or instead of the cladding being disposed about the outer surface of the suction tube the cladding may be disposed about the internal surface of the optical waveguide such that the cladding is disposed between the suction tube and the internal surface of the optical waveguide. Optionally the suction tube is made from appropriate light conducting materials such that the walls of the suction tube form the optical waveguide. Optionally a separate suction tube and waveguide are not necessary. The internal and/or external surfaces of the suction tube/optical waveguide may feature a cladding layer.

Optionally the cross sectional area of the optical waveguide may change from the proximal end to the distal end thereof, and wherein the optical waveguide comprises a pocket or receptacle for receiving the suction tube. The pocket or receptacle may comprise a concave region. Also, optionally, the illuminated suction apparatus may further comprise one or more extraction features near the distal end of the outer surface of the optical waveguide, wherein the extraction features extract the light conducted by the optical waveguide and project the extracted light to illuminate a surgical field.

Aspects of the disclosure provide a surgical illumination system for illuminating a surgical field, the surgical illumination system comprising an optical fiber and an optical tip. The optical tip comprises a bore, wherein the optical fiber is disposed in the bore. The optical tip further comprises an output zone having a plurality of microstructures for directing light away from the optical tip towards the surgical field. A portion of the bore comprises a cladding layer. Alternatively, the cladding layer may be disposed about a surface of a portion of the optical fiber that is disposed in the bore. The cladding layer may comprise one or more of the following materials: fluoro acrylate, a fluoro methylacrylate, or polytetrafluoroethylene (PTFE) and may have a thickness of at least 350 nanometers. The cladding layer circumferentially clads the optical fiber within the bore such as to promote TIR of light within the optical fiber. In many embodiments, the plurality of microstructures comprises a plurality of prisms, the prisms configured to refract light passing through. The microstructures may also comprise one or more facets.

Aspects of the disclosure provide a surgical illumination system for illuminating a surgical field, the surgical illumination system comprising a cannula having a proximal end, a distal end, a bore therebetween that proceeds along a longitudinal axis of the cannula, an inner surface, and an outer surface. The cannula is typically formed by a polymeric material and the bore is sized and dimensioned to accommodate one or more surgical instruments. The surgical illumination system further comprises an optical waveguide adapted to conduct light via TIR from the proximal end of the cannula to the distal end of the cannula. The optical waveguide may comprise COP, COOP, or other cyclo olefin materials or other optical materials known in the art. The surgical illumination system may also comprise one or more light extracting structures near the distal end of the cannula configured to extract the conducted light from the optical waveguide and direct the extracted light to the surgical field. In some embodiments, the light extracting structures may comprise: one or more circumferential facets formed at an obtuse angle to an adjacent cannula surface. Optionally the surgical illumination system further comprises an optical cladding layer. The light extracting structures may be disposed on the inner surface, the outer surface, or both of the inner and outer surfaces.

The optical waveguide may comprise a receiving portion configured to receive light. The received light may then be conducted to the surgical field by the optical waveguide in order to illuminate the surgical field. The received light typically comes from a light source, the light source being optically coupled to the receiving portion. The light source may comprise a light emitting diode (LED), incandescent bulb, xenon flash lamp, laser, combinations thereof, or any other light source known in the art. Optionally the light source is disposed upon or within the receiving portion of the waveguide. For example, the light source may comprise a LED that is disposed within the optical waveguide at the receiving portion, thereby allowing light emitted from the LED (or any other light source) to enter the optical waveguide at the receiving portion and to be conducted by the optical waveguide. The light source may also be disposed on or adjacent a surface of the receiving portion such that light emitted from the light source enters the optical waveguide through the surface of the receiving portion.

Optionally, the light source may be optically coupled to the receiving portion of the optical waveguide by a flexible input (also referred to as a "pigtail" or "pigtail connection"). The pigtail typically comprises a light conducting material configured to conduct light from the light source to the receiving portion of the optical waveguide. The pigtail may comprise one or more optical fibers. The pigtail may comprise a plurality of optical fibers. The plurality of optical fibers may be arranged into one or more bundles. Each bundle may comprise a fiber optic ribbon or cable. The plurality of optical fibers of each bundle may be arranged such a cross section of each bundle shows the optical fibers arranged in one or more patterns. The one or more patterns may include concentric circles, concentric hexagons, and/or rectangles. One or more of the optical fibers of the one or more bundles may comprise an optical cladding. The pigtail may comprise multiple bundles (also referred to as "cables") that are connected by optical connectors. The pigtail may be optically coupled to the receiving portion of the optical waveguide via one or more of the following: an optical connector (or adapter), an end-to-end ("butt" or "abutting") coupling between the pigtail's light conducting material and a surface of the optical waveguide's receiving portion, and/or a portion of the pigtail that protrudes into the optical waveguide.

As mentioned above, several aspects of the disclosure describe a flexible input or "pigtail" comprising one or more bundles of optical fibers. In embodiment described throughout this application, the optical fibers of the flexible input may be splayed at one or more portions of the flexible input in one or more dimensions to thereby more evenly distribute the optical fibers throughout the optical waveguide's receiving portion. The optical fibers may be splayed to form a distribution of fibers shaped to conform to cross section of optical waveguide or receiving portion thereof. For example, for a cylindrical cannula having its proximal end as a receiving portion, the distal end of a flexible input may be splayed into a cylinder such that the proximal end of the optical waveguide and the distal end of the input portion have matching cross sections when they are mated to form an optical coupling. In some embodiments, when the optical fibers are splayed they may be formed into, joined by, or integrated into a shaped portion of light conducting material. This thereby allows the splayed fibers to maintain their splayed configuration.

The optical cladding layer typically comprises one or more of the following materials: fluoro acrylate, a fluoro methylacrylate, or polytetrafluoroethylene (PTFE), has a thickness greater than 350 nanometers, and is configured to prevent or minimize evanescent waves of the conducted light from coupling to a medium adjacent the optical waveguide. Optionally the surgical illumination system comprises one or more light conducting conduits integrated into the proximal end of the cannula for introducing light into the optical waveguide. Optionally the wall of the cannula forms the optical waveguide.

The optical waveguide may comprise a plurality of light directing elements formed into the surface of the cannula for directing light from the proximal end to the distal end of the cannula. Optionally the light directing elements comprise one or more prisms formed in the outer surface of the cannula, wherein the one or more prisms are oriented parallel to the longitudinal axis of the cannula.

Any of the optical claddings described herein may comprise a mask pattern, wherein the mask pattern provides one or more uncladded regions within one or more areas covered by the optical cladding (optical cladding layer).

Any of the optical claddings (also referred to as cladding layer, or optical cladding layer) described herein may comprise one or more additional layers. The one or more additional layers may comprise materials that augment or modify the optical properties of the optical cladding. The one or more additional layers may comprise materials that augment or modify one or more physical properties of the optical cladding or waveguide covered thereby. Such physical properties may include but are not limited to one or more of the following: durability, hardness, surface porosity, reflectance, electrical conductivity, thermal conductivity, the ability to support or hinder microbial growth, one or more magnetic properties, surface texture, and hydrophobicity. The augmentation or modification of any or all of these properties may also be accomplished by a single layer cladding or by multiple layers of cladding. The coating in this embodiment as well any of the other embodiments may modify other optical properties such as by providing an anti-reflection coating. The cladding in this or any of the embodiments disclosed in this specification may have multiple layers to compose other properties. Optionally the cladding may have a single layer that has multiple functions such as providing a desired index of refraction to preserve total internal reflection and to provide a hydrophobic coating.

Another aspect of the disclosure provides a method of illuminating a surgical field, the method comprising providing a surgical instrument, having a non-fiber optic waveguide integrated therewith. The optical waveguide may comprise an input and an output and may be configured to conduct light between the input and the output via total internal reflection. The method may further comprise cladding the optical waveguide with a layer of cladding material having a thickness of at least 350 nanometers thereby preventing or minimizing frustrated total internal reflection of the conducted light. The surgical instrument may be selected from one or more of the following: a surgical retractor, a suction device, a cannula, and an optical tip. Optionally the waveguide comprises COP or a copolymer thereof. The cladding material may comprise one or more of a fluoro acrylate, a fluoro methylacrylate, or polytetrafluoroethylene (PTFE).

In any of the embodiments disclosed in this application, the cladding material may optionally comprise a polytetrafluoroethylene (PTFE) including but not limited to one or more of the following: tetrafluoro ethylene, Teflon PTFE, Fluon PTFE, Syncolon PTFE, Hyflon, Cytop, Poly(1,1,2,2-tra fluoroethylene).

In any of the embodiments disclosed in this application, the cladding material may optionally comprise a fluorinated ethylene propylene (FEP) including but not limited to one or more of the following: hexafluoropropylene, Teflon FEP, Neoflon FEP, or Dynon FEP.

In any of the embodiments disclosed in this application, the cladding material may optionally comprise a perfluoroalkoxy (PFA) including but not limited to one or more of the following: perfluoroether, perfluoropolyether, perfluoroalkoxy alkane, perfluoroalkyl, Krytox PFA, or Nafion PFA.

In any of the embodiments disclosed in this application, the cladding material may optionally comprise an ethylene tetrafluoroethylene (ETFE) including but not limited to one or more of the following: poly (ethene-co-tetrafluroethene), Tezfel, Fluon ETFE, Neoflon ETFE, or Texlon.

In any of the embodiments disclosed in this application the cladding material may comprise a polychlorotrifluoroethylene (PCTFE) including but not limited to one or more of the following: polymonochlorotrifluoroethylene, poly(vinyl trifluorochloride), poly(trifluoroethylene chloride), poly(trifluorochlorethene), poly(chlorotrifluoroethene), chlorotrifluoroethylene, Kel-F 81, Kel-F 300, Neolfon PCTFE, Aclon, Aclar, Hostaflon C2, Fluon PCTFE, Voltalerf, Hostafflon C, or Plaskon.

In any of the embodiments disclosed in this application the cladding layer may comprise a polyvinylfluoride (PVF) including but not limited to one or more of the following: Tedlar, vinyl fluoride, polyvinylidene fluoride (PVDF), polyvinylidene difluoride, Kynar, Hylar, Solef, or Sygef.

In any of the embodiments disclosed in this application the cladding material may comprise a polyethylenechlorotrifluoroethylene (ECTFE) including but not limited to Halar ECTFE. In any of the embodiments disclosed in this application the cladding material may comprise a perfluorinated elastomer (FFPM/FFKM) including but not limited to one or more of the following: Kalrez, Tecnoflon PFR, or perfluorocarbon rubber.

In any of the embodiments disclosed in this application the cladding layer may comprise a fluorocarbon [chlorotrifluoroethylenevinylidenefluoride] (FPM/FKM) including but not limited to one or more of the following: Vicon, Tecnoflon VFM, Ffuoronated hydrocarbon, Fluorel, Chemraz, or Kalrez FKM.

In any of the embodiments disclosed in this application the cladding layer may comprise a perfluoropolyether (PFPE) including but not limited to one or more of the following: Krytox, Fomblin, or perfluoropolyether triethoxysilane.

In any of the embodiments disclosed in this application the cladding layer may comprise a fluoro silicone (FVMQ) including but not limited to one or more of the following: perfluoro alkyl fluorosilane, fluorinated silicone rubber, fluorosilicone rubber, perfluoro triethoxylilane, fluorosilane, Nusil, or FluoroSyl.

In any of the embodiments disclosed in this application the cladding layer may comprise a fluoro acrylate including but not limited to one or more of the following: fluoro methacrylate, Raymat 137, UV Opticlad, polymer cladding, acrylate matrix, FluorAcryl, Cytonix, MY Polymer, or FluorN.

In any of the embodiments disclosed in this application the cladding layer may comprise a fluorourethane alkyd including but not limited to fluorothane.

Optionally, a surgical illumination system comprises a non-fiber optic optical waveguide for illuminating a surgical field, and a surgical instrument coupled to the non-fiber optic optical waveguide. The surgical instrument having an optical cladding disposed over at least portion thereof. The optical cladding is disposed between the waveguide and the surgical instrument and the optical cladding helps preserve total internal reflection in the waveguide. The cladding may be 350 nanometers or greater in thickness, or the cladding may comprise a fluoro polymer.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 1A-1C show various optical waveguides having cladding layers.

FIGS. 40, 41A-41B, and 42A-42B depict a fiber optic ribbon and cable arrangement for a flexible input to an optical waveguide.

DETAILED DESCRIPTION OF THE INVENTION

Figure 1D:
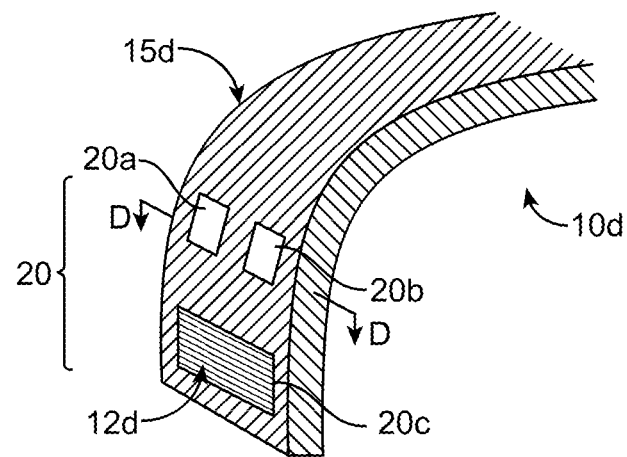
FIG. 1D shows an optical cladding that has been applied in a masking pattern.

FIGS. 1A-1C illustrate various optical waveguides for illuminating a surgical field. The waveguides are integrally formed as either a surgical tool or a part thereof. Each waveguide comprises a polymer material adapted to conduct light via total internal reflection (TIR). Typically the polymer may comprise acrylic, polycarbonate, cyclo olefin polymers or copolymers thereof but one of skill in the art will appreciate that other materials may also be used. FIG. 1A shows an illuminating tissue retractor waveguide 10a, which is shaped like a hook for engaging tissue to thereby provide a retraction force. Waveguide 10a comprises input 13a for receiving light from a light source such as a fiber optic cable (f.o.) or a LED. Cladding layer 15a enhances TIR and prevents or minimizes evanescent waves of the light being conducted through the waveguide from coupling to or leaking into the surrounding environment, such as adjacent instruments, implants, tissue, blood, or other bodily fluids. In preferred embodiments, the cladding layer(s) comprises a 350 nanometer or thicker layer of one or more of the following materials: a fluoro polymer such as fluoro acrylate, a fluoro methylacrylate, or polytetrafluoroethylene (PTFE). Other materials are also known in the art. Such a cladding layer promotes TIR by preventing or minimizing evanescent waves of the transmitting light in the light guide from coupling into the immediate environment or the retractor. The cladding layer(s) may further comprise layers of additional materials such as adhesive materials, anti-reflection materials, or hydrophobic materials. Cladding layer 15a (or 15b or 15c) may be disposed on a portion of, or all of the waveguide boundary surfaces 11a, 11b, or 11c. Light 18 may leave or exit the waveguide at output surfaces 14a, 14b, and 14c. Light may also exit the waveguide via extraction surfaces 12a, 12b, 12c. Optionally the output surfaces 14a-14c may be replaced by reflective surfaces so all light exits through extraction surfaces 12a-12c. The extraction surfaces may comprise one or more angled facets positioned and oriented to prevent TIR. The location of cladding surfaces may be chosen strategically. For example, one of the cladding surfaces on the tissue retractor waveguide 10a is located on a distal "hook" portion 19a, the portion intended to engage tissue (not shown). The cladding surface may then prevent light from coupling and leaking into the tissue.

FIG. 1B shows a tubular illuminating cannula waveguide 10b, with input 13b cladding layers 15b on both the external and internal boundary surfaces of the cannula tube. Bore 16b is typically sized to a diameter D to accept surgical tools. FIG. 1C shows a distal portion of an illuminating suction tool 10c. An input element such as 13a or 13b is provided but not shown. Cladding surfaces (layers) 15c are strategically located at bends in the waveguide material where light leakage is more problematic due to a shift in the angles required for TIR. Bore 16c is adapted to be coupled to a vacuum or suction source (not shown) to provide suction of the surgical field SF while the conducted light 18 exits waveguide 10c via output 14c and/or extraction surfaces 12c to illuminate the surgical field. Optionally, the tubular cannula may be constructed from two half cylinders which may be glued together or otherwise attached to one another. One or more cladding layers may be disposed between the half cylinders where they mate together to retain conducted light within each respective half.

In any of the embodiments provided throughout this application that comprise an optical cladding, the optical cladding may comprise a mask pattern. The mask pattern may feature areas of exposed waveguide surface within or disposed around areas of cladded waveguide surface. FIG. 1D, shows a waveguide 10d having optical cladding 15d. In area 20 the cladding 15d is applied in a mask pattern the mask pattern comprises one or more areas 20a, 20b, and 20c where the waveguide's surface 11d is exposed. The one or more areas of exposed waveguide surface 11d may comprise light extraction features such extraction features 12d shown in area 20c.

Figure 1E:
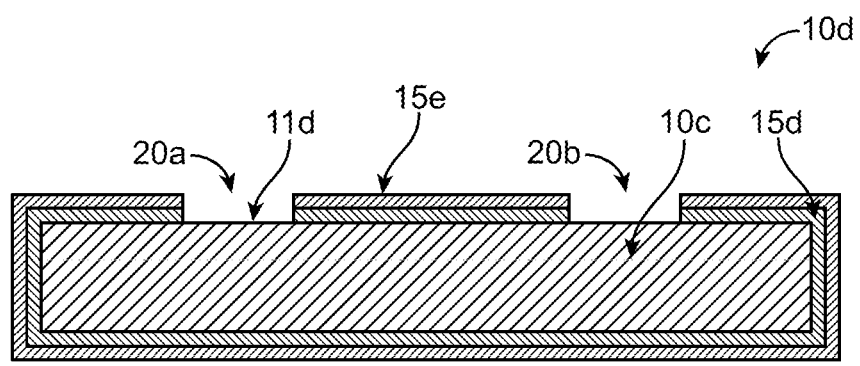
FIG. 1E is a cross section taken along D-D from FIG. 1D and shows an optical cladding with one or more layers.

Any embodiments described/provided throughout this application that comprise an optical cladding may further comprise one or more additional layers to the optical cladding. The one or more additional layers may comprise materials that augment or modify optical or other properties of the cladding and/or waveguide. FIG. 1E shows a cross section of the waveguide 10*d* taken at segment D. The waveguide's light conducting material 10*e* is shown along with a multi-layer optical cladding 15*d* having a second layer 15*e*. Exposed waveguide is shown in areas 20*a* and 20*b*. Second layer 15*e* may augment or modify the optical properties of the cladding layer. Second layer 15*e* may augment or modify other properties of the cladding layer or waveguide. For instance the second layer may modify a surface porosity, hydrophobicity, smoothness, durability, hardness, and/or reflectivity. In one example, second layer 15*e* may make the optical cladding super-hydrophobic to help repel blood or other fluids.

One aspect of the present disclosure provides retractor/waveguide surgical illumination systems featuring one or more claddings that promote TIR in order to improve lighting efficiency and performance. Further details of retractor/waveguide surgical illumination systems may be found in U.S. patent application Ser. Nos. 11/634,874 and 11/923,483 now U.S. Pat. Nos. 8,409,088 and 8,088,066, respectively, the entire contents of each of which are hereby incorporated by reference. Further details pertaining to waveguides and their materials may be found in U.S. patent application Ser. No. 13/026,910, which is hereby incorporated by reference in its entirety.

Figure 2:
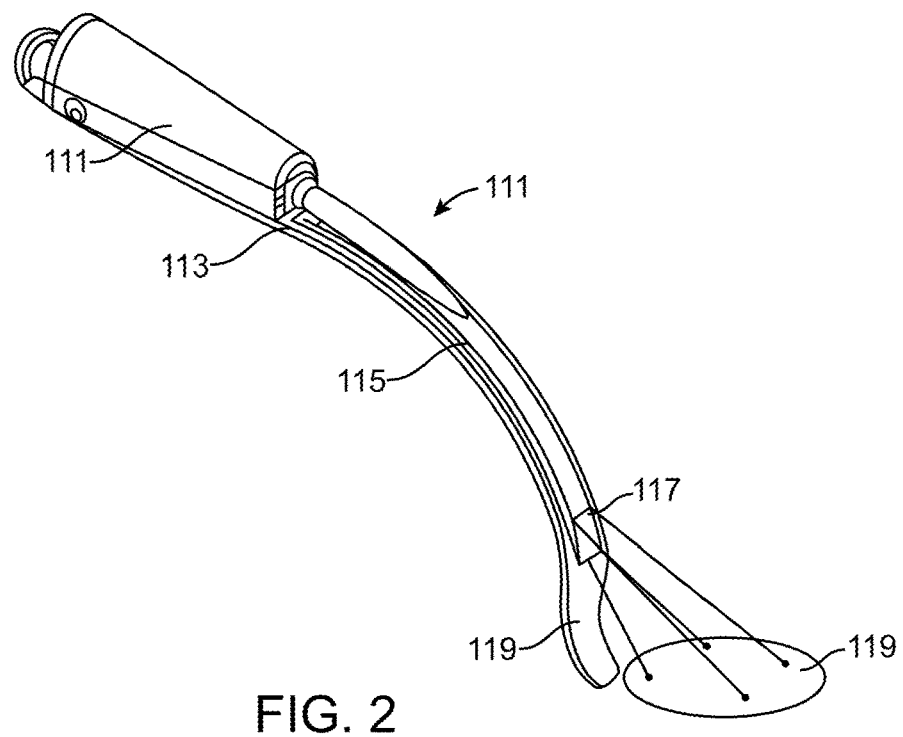
FIG. 2 is a surgical retractor blade fitted with an attachable illuminator and light source.
Figure 3:
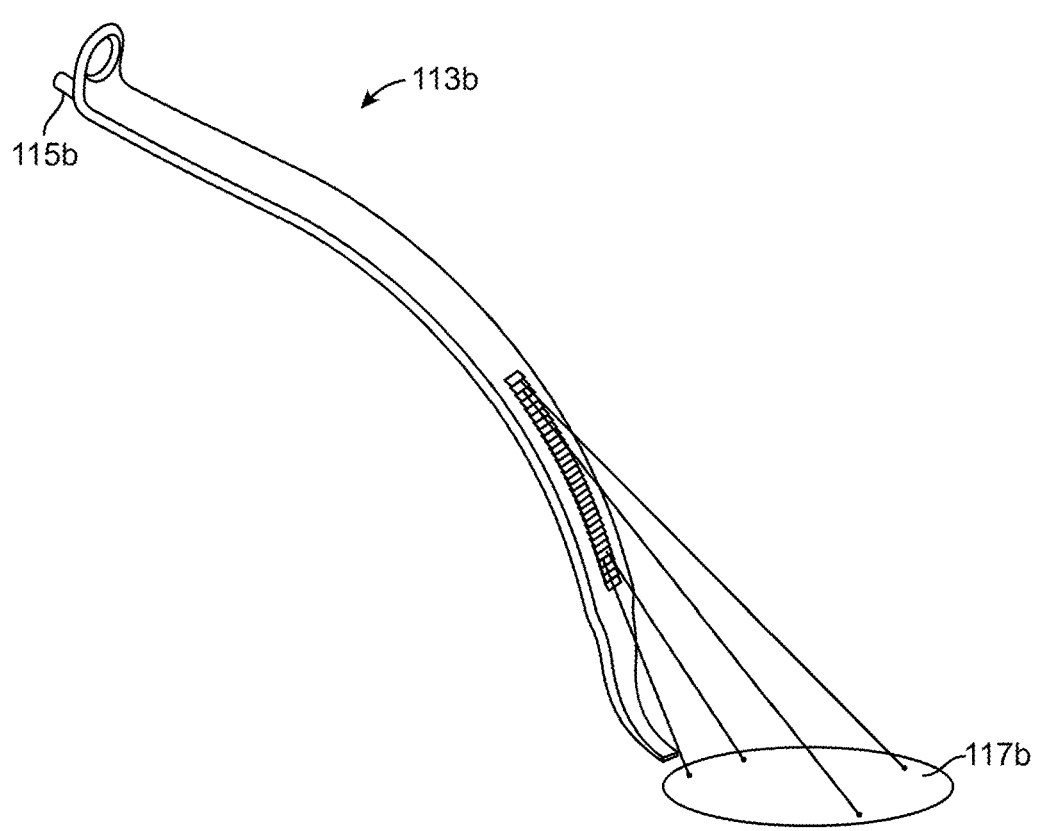
FIG. 3 is an integrated illuminating retractor wherein the light guide is shaped to match the form and function of a standard retractor.

FIGS. 2 and 3 illustrate a retractor illumination system implemented by modification of a typical retractor. In FIG. 2, retractor 111 is fitted with an optical waveguide (also referred to as "light guide") insert 115 which is mounted on the retractor 113, such that a light emitting surface 117 of the light guide faces the open surgical field 119. The light guide insert 115 may be mounted on the front surface of the retractor, or it may be mounted on the back side of the retractor, so long as a light emitting portion 117 of light guide 115 is exposed to illuminate surgical field 119, for example, through a cut out formed in the retractor or from around one or more sides of the retractor. Light guide insert 115 of FIG. 2 may be formed of any suitable material such as transparent or translucent material, shaped to conform to the surface of retractor 113 and includes one or more mating structures for releasable or fixed attachment to the retractor. In preferred embodiments light guide 115 comprises COP (or COCP). A light source 111 may be mounted on the proximal end of the retractor, in optical communication with the light guide, and may be a small self-contained LED light engine mounted on the handle portion of the retractor, as shown, or a fiber optic cable carrying light from a remote laser or other suitable light source. In some embodiments the light source 111 may be mounted directly on or within the light guide 115; this may be preferred if the light source comprises one or more LEDs. A cladding layer (not shown) may be applied to at least a portion of the surface of light guide 115, such a cladding layer would not cover light emitting portion 117. Preferably, the cladding layer comprises a 350 nanometer or thicker layer of one or more of the following materials: fluoro acrylate, a fluoro methylacrylate, or polytetrafluoroethylene (PTFE). Such a cladding layer promotes TIR by preventing or minimizes evanescent waves of the transmitting light in the light guide from coupling into the immediate environment or the retractor.

Figure 4:
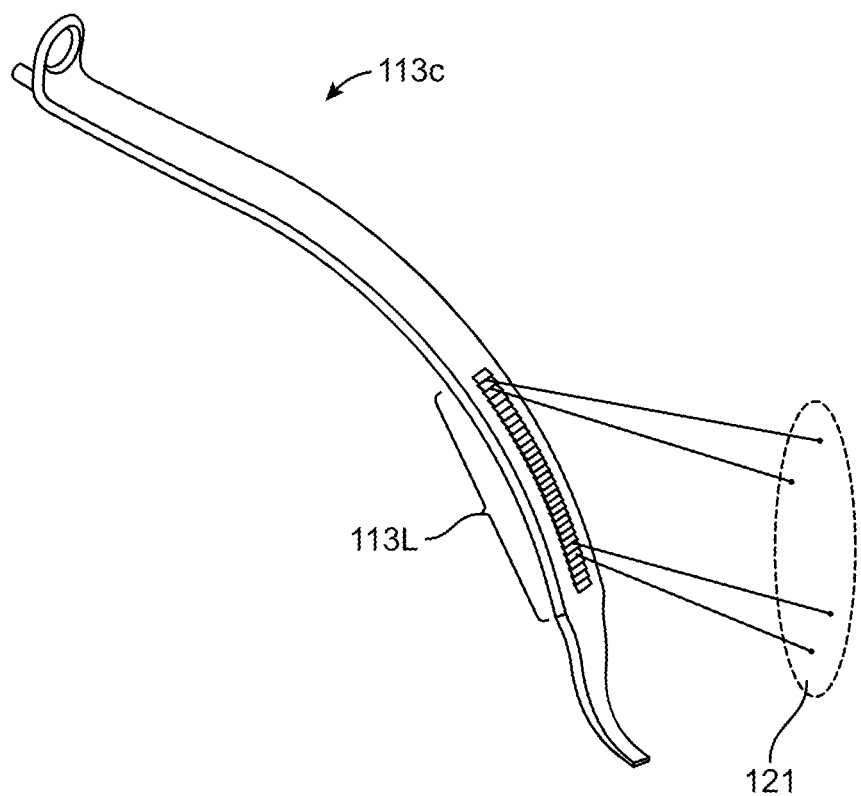
FIG. 4 is the integrated illuminating retractor of FIG. 2 with an alternatively configured light guide.

In FIG. 3, integrated illuminating retractor 113*b* is fabricated from a suitable light guide material, such as COP or COCP and a light source is operably connected to an input aperture 115*b* provided on the proximal handle portion of the retractor. The light guide, whether distinct from the retractor or integrally formed as a retractor, is modified at various portions along its length to emit and direct light to a nominal illumination field, such as surgical field 117*b* which is near the distal blade portion of retractor 113*b* when in use. The nominal illumination field is based on the particular retractor type and general surgical procedure in which the retractor will be used. In an operation such as total hip arthroplasty, during broaching for example, the surgical field will include the femoral neck, and the surgical field will be as illustrated in FIG. 2, above the hook 119 of the retractor and below the light emitting section, and on a plane substantially perpendicular to the long axis of the lower portion of the retractor. In other surgeries, it may be required to direct light to a plane substantially below the tip of the retractor (for example, surgical field 117*b* as shown in FIG. 3) or substantially parallel to lower portion 113L of retractor 113*c* (for example, surgical field 121 as shown in FIG. 4).

Figure 5:
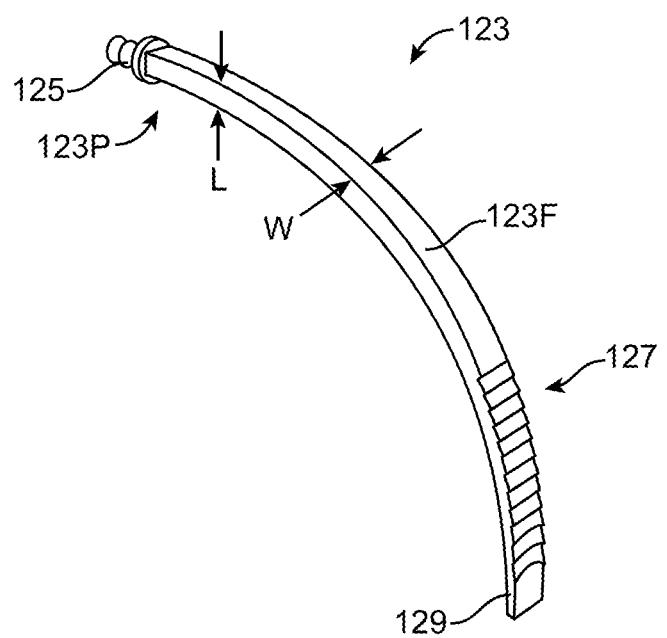
FIG. 5 is a light guide with an input and light directing structures on the front and back surfaces.
Figure 6:
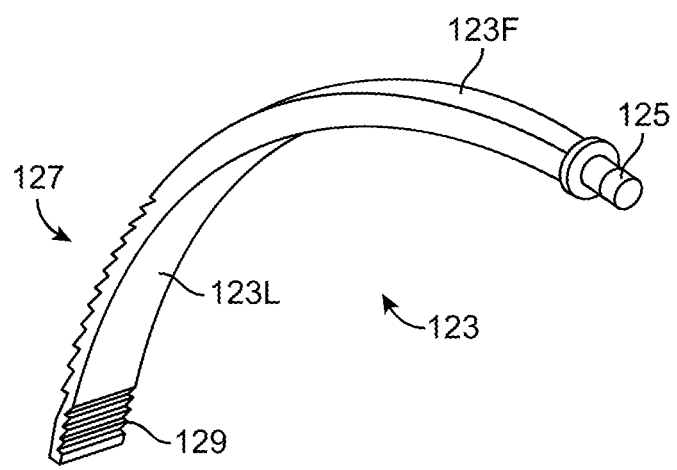
FIG. 6 is a rear perspective view of the light guide of FIG. 4 showing the rear light directing structures.

FIGS. 5 and 6 show a light guide 123 for use as a light guide insert (as in FIG. 2) or, if made of rigid and tough material such as a polycarbonate, as a simple hook retractor or blade retractor. The light guide proximal end 123P includes a light receiving aperture 125 which is adapted to be optically coupled to a light engine or a fiber optic bundle fed by a higher power light source. A portion of the blade, on the front surface 123F of the blade, may be faceted with one or more facets such as facets 127, which permit light passing through the light guide to be directed onto a surgical field. Each facet may be considered to be in the form of a stair step with a riser surface such as surface 127R and a step surface such as surface 127S.

The step surface generally supports total internal reflection whereas the riser surface is typically the light emitting surface. Refraction of the light at the riser surface of the facet (typically air is the other medium) results in significant change of direction of the light emerging from each facet, so the facets are angled, relative to the axis of the device and the surgical field, to refract light toward the surgical field. The angle between the step surface and the riser surface may be chosen to maximize light directing and light extracting functions for each facet, and this angle may be different from facet to facet. While the riser and step surfaces are typically flat, they may also have more complex shapes to control light within the light guide or to direct light out of the light guide. For example, the riser surface may include microstructures to shape the light exiting that surface. Laterally, each riser may be straight or may have some other shape, such as convex or concave. The spacing of the stepped facets along the light guide may be described by a mathematical formula and or may be irregular or aperiodic. The size of the facets may be regular or irregular along the light guide. In addition, the step surface may be coated, for example, with a metallic reflective coating, to promote total internal reflection.

By providing numerous facets, the surgical field may be illuminated with numerous rays and may appear to be uniformly illuminated. Fewer facets may be used but may result in some areas receiving more illumination than other areas, which may or may not be desirable. A single facet may be used, for example, by cutting off the end of the light guide, but this approach lacks the light directing capabilities of the configurations described herein. Light directing capabilities of such a single facet may be improved by shaping the facet, for example, angling the face or providing a concave or convex face, and or by adding micro-structures to shape the profile of the light beam.

Figure 7:
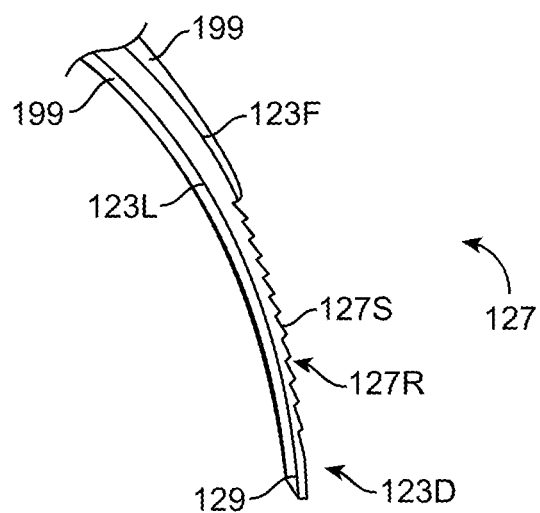
FIG. 7 is a sectional view of the light guide of FIG. 4 showing the stepped facets of the light directing structures.

The back side of the light blade, lower surface 123L, near the distal tip 123D, may include angled facets 129 to cause internal reflections of light rays remaining in the light guide, reflecting those rays toward the surgical field at an angle to the front surface (at the distal tip) sufficient to permit passage of those light rays past the surface of the light guide (without all being reflected back into the light guide). The light guide front surface at the distal tip may have additional light directing structures, such as a molded or foil-stamped micro-structure diffuser or diffusing film. Again, numerous facets are provided, and the angles of the reflecting surface of the back facets are selected, relative to the incoming light and the surgical field, to create a uniform illumination. FIG. 7 provides a side view of light guide 123, illustrating the placement of the facets 127 and 129 and rough angles of the diffracting and reflecting faces of the facets. FIG. 7 also shows cladding layers 199 that may be disposed on surfaces 123L and 125F (but preferably not facets 127) to promote TIR within the light guide to increase optical efficiency. Such cladding layers are described in more detail, elsewhere in this application.

The faceted area may vary, depending on the application. For the retractors illustrated, faceted areas of about 10 to 30 mm long, and 10 to 30 mm wide, are provided. This provides good illumination for many typical surgeries. The faceted areas are not limited to these dimensions and may comprise any dimensions appropriate for a given illumination application. One or more facets may be placed at different zones along the light guide to illuminate different parts of the surgical field, and the facets in each of these zones may have different design characteristics to meet illumination needs. For example, it may be desirable to have one part of a surgical field illuminated with a focused beam to create a bright spot whereas another part of the surgical field may require a more diffuse illumination. Alternatively, it may be desirable to have the light directed to the side so that the retractor may be placed in one area but illuminate a nearby area that is off to the side of the retractor. Though shown in very large scale in the drawing, the preferred size of the facets is about 25 to 500 microns, more preferably about 50 microns, which will provide illumination without perceptible dark and light bands on the surgical field. The facets may be curved, as shown, in the manner of Fresnel facets (though the function is to redirect light rays parallel to the plane of the light guide) to focus the escaping light onto a particular area or more narrowly defined nominal surgical field. Each facet distal face is angled differently, depending on its position on the light guide and the desired illumination field. The actual angles to be used are dependent on the particular retractor, the particular light guide material, the light guide geometry, and the geometry of the desired illumination zone.

Placement and design of facets and the features that support total internal reflection may need to be altered for a substantially flat light guide versus a substantially curved light guide or a light guide with both flat and curved geometries. Facets may be provided only on the front face or only on the rear face, or both depending on the illumination needs. The combination of light control features described herein improves the overall efficiency of the light guide by ensuring that most of the light in the light guide is directed toward the surgical field. For example, we have found that the light guide of FIG. 5, when fabricated from silicone, has greater than 65 percent efficiency as compared to less than 40 percent efficiency for optical fiber based devices. In addition, other features are normally included as part of efficient light guide design, such as a surface roughness less than 500 Angstroms in variation, preferably less than 100 Angstroms, in order to maximize total internal reflection and minimize light loss in the light guide itself, both of which contribute to overall efficiency. Lower absorption materials and/or coatings, such as reflective coatings or films, are also preferred to maximize efficiency. Additional design elements may be included in the light guide to maximize efficiency, that is, to maximize the ratio of the amount of light illuminating the target area to the amount of light entering the light guide at its input. It is preferred that the light emitting structures be designed to minimize light directed back up into the surgeon's eyes to minimize eye fatigue and perceived glare.

The dimensions of light guide 123 in FIG. 5 change along its length. The thickness T decreases from input 125 (proximal) to the opposite tip (distal). The stepped facets serve to remove material, making light guide 123 thinner toward the distal end 123D to minimize its impact on the surgical work space and not hinder the surgeon's ability to manipulate instruments within that space. Light guide 123 gets wider along dimension W from the proximal to distal ends. This improves the ability to generate a wider beam. In another embodiment the light guide may be made to taper distally, in excess of any material reduction that may be caused by light directing structures. This causes the numerical aperture to increase as the area decreases. The angle of some of the light thus increases, which can be used to advantage to create a wider beam. Thus, the cross-section of a light guide may be changed from proximal to distal ends to improve light directing capabilities.

The device is illustrated with a flat blade retractor, but it may be implemented in various forms including Steinman pins, cylindrical spinal retractors, hooks, converse blade retractors, right angle retractors, Desmarres lid retractors, lumbar retractor blades, laryngoscope blades, malleable retractors (provided the light guide is malleable or flexible), dental retractors and various other retractors. The facets may be formed as ridges, steps, or distally facing shoulders cut into or built up upon the face of the light guide.

Figure 8:
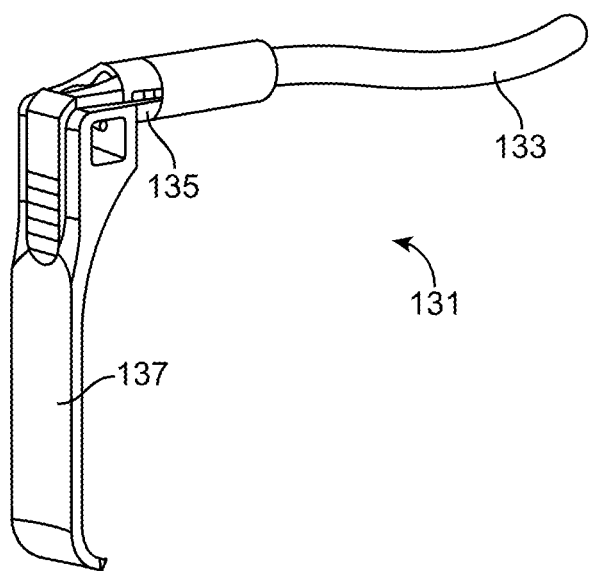
FIG. 8 is a light guide releasably attached to a right angle retractor blade with a fiber optic cable attached to the light guide.

FIG. 8 shows a retractor blade illuminator 131 with fiber optic cable 133 shown connected to light guide 135 that is releasably attached to right angle blade retractor 137. Any suitable right angle blade retractor may be used such as McCulloch, Caspar, Taylor, Meyeding or any other. In this illustration a narrow McCulloch style retractor is shown. Light guide 135 may be scaled to any size of blade retractor. The fiber optic cable has a male connector and the light guide has a corresponding female connector, but the opposite arrangement may also be used. Coupling of light from the fiber optic cable to the light guide is typically through a simple face-to-face coupling, typically with a small air gap between the two faces. The coupling interface may also be accomplished with an index matching material to facilitate light transfer. In some applications, it may be desirable to include other elements in the coupling interface such as focusing lenses or protective sapphire windows. In some embodiments the waveguide forms the retractor blade itself instead of attaching to separate retractor blade. Typically in such embodiments the waveguide comprises a cladding layer that provides enough strength and/or rigidity such the waveguide/cladding can directly contact and support the tissue being retracted.

Figure 9:
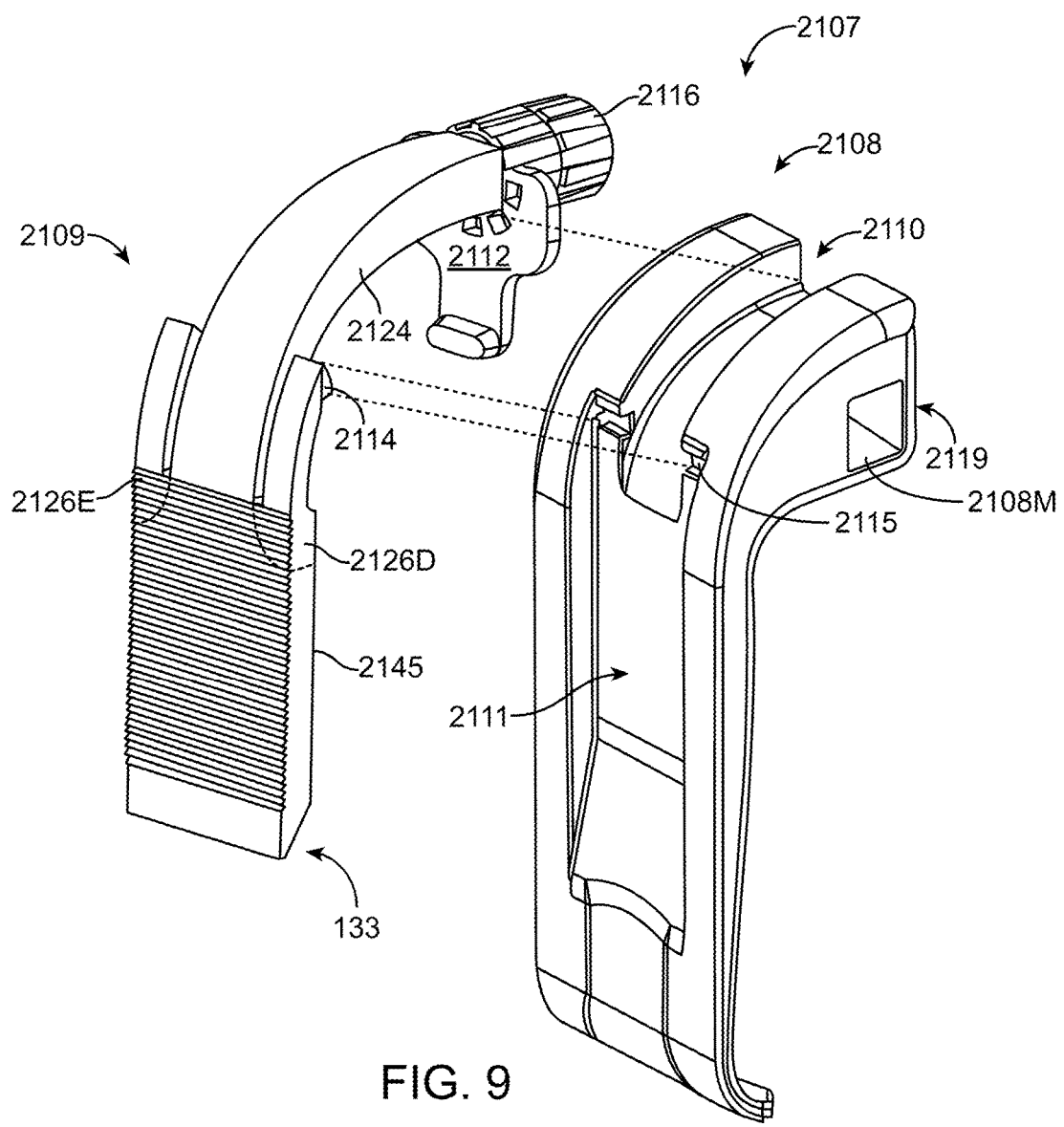
FIG. 9 is a perspective view of an illuminated retractor.
Figure 9A:
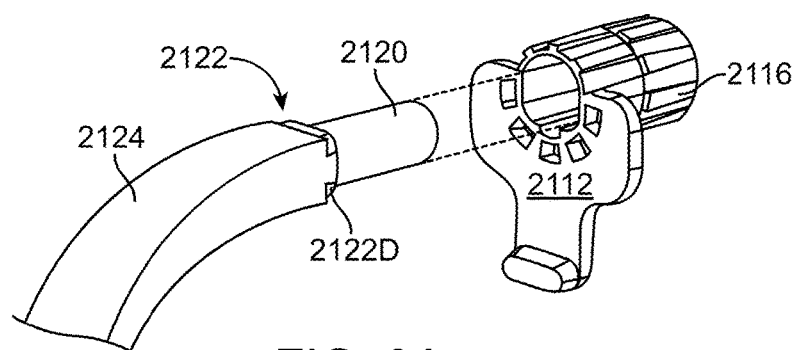
FIG. 9A is an exploded view of the input collar and the illumination blade input.

Illuminated retractor 2107 as illustrated in FIG. 9 is composed of retractor blade 2108 and illumination blade 2109. Retractor blade 2108 is shown as a McCulloch style retractor blade for use with a McCulloch retraction system although any suitable retractor and or retraction configuration may be used. Retractor blade 2108 includes one or more mechanical connectors such a mechanical connector 2108M and neck slot or channel 2110 to accommodate neck zone 2124 and blade slot 2111 to accommodate output blade 2125 within retractor blade 2108 while maintaining an air gap between active zones of the illumination blade and the retractor. Two or more engagement elements such as blade or plate 2112 and tabs 2114 secure illumination blade 2109 to retractor blade 2108. Each tab 2114 engages one or more engagement receptacles such as receptacles or recesses 2115. Plate 2112 is joined to collar 2116, and when collar 2116 removably engages input dead zone 2122D, the collar surrounds illumination blade input 2118. The removable engagement of collar 2116 to input dead zone 2122D also brings plate 2112 into contact with end surface 2119 of the retractor blade. Collar 2116 securely engages dead zone 2122D and surrounds cylindrical input zone 2120 and forms input air gap 2120G. Engagement at dead zones minimizes interference with the light path by engagement elements such a plate 2112 and tabs 2114. Plate 2112 engages end surface 2119 and tabs 2114 resiliently engage recesses 2115 to hold illumination blade 2109 fixed to retractor blade 2108 without contact between active zones of illumination blade 2109 and any part of retractor blade 2108.

Illumination blade 2109 is configured to form a series of active zones to control and conduct light from illumination blade input 2118 of the cylindrical input zone 2120 to one or more output zones such as output zones 2127 through 2131 and output end 2133 as illustrated in FIGS. 9, 9A, 10, 11 and 12. Illumination blade 2109 also includes one or more dead zones such as zones 2122D, 2126D and 2126E. Dead zones are oriented to minimize light entering the dead zone and thus potentially exiting in an unintended direction. As there is minimal light in or transiting dead zones they are ideal locations for engagement elements to secure the illumination blade to the retractor.

Light is delivered to illumination blade input 2118 using any conventional mechanism such as a standard ACMI connector having a 0.5 mm gap between the end of the fiber bundle and illumination blade input 2118, which is 4.2 mm diameter to gather the light from a 3.5 mm fiber bundle with 0.5 NA. Light incident to illumination blade input 2118 enters the illumination blade through generally cylindrical, active input zone 2120 and travels through active input transition 2122 to a generally rectangular active retractor neck 2124 and through output transition 2126 to output blade 2125 which contains active output zones 2127 through 2131 and active output end 2133. Retractor neck 2124 is generally rectangular and is generally square near input transition 2122 and the neck configuration varies to a rectangular cross section near output transition 2126. Output blade 2125 has a generally high aspect ratio rectangular cross-section resulting in a generally wide and thin blade. Each zone is arranged to have an output surface area larger than the input surface area, thereby reducing the temperature per unit output area.

Figure 10:
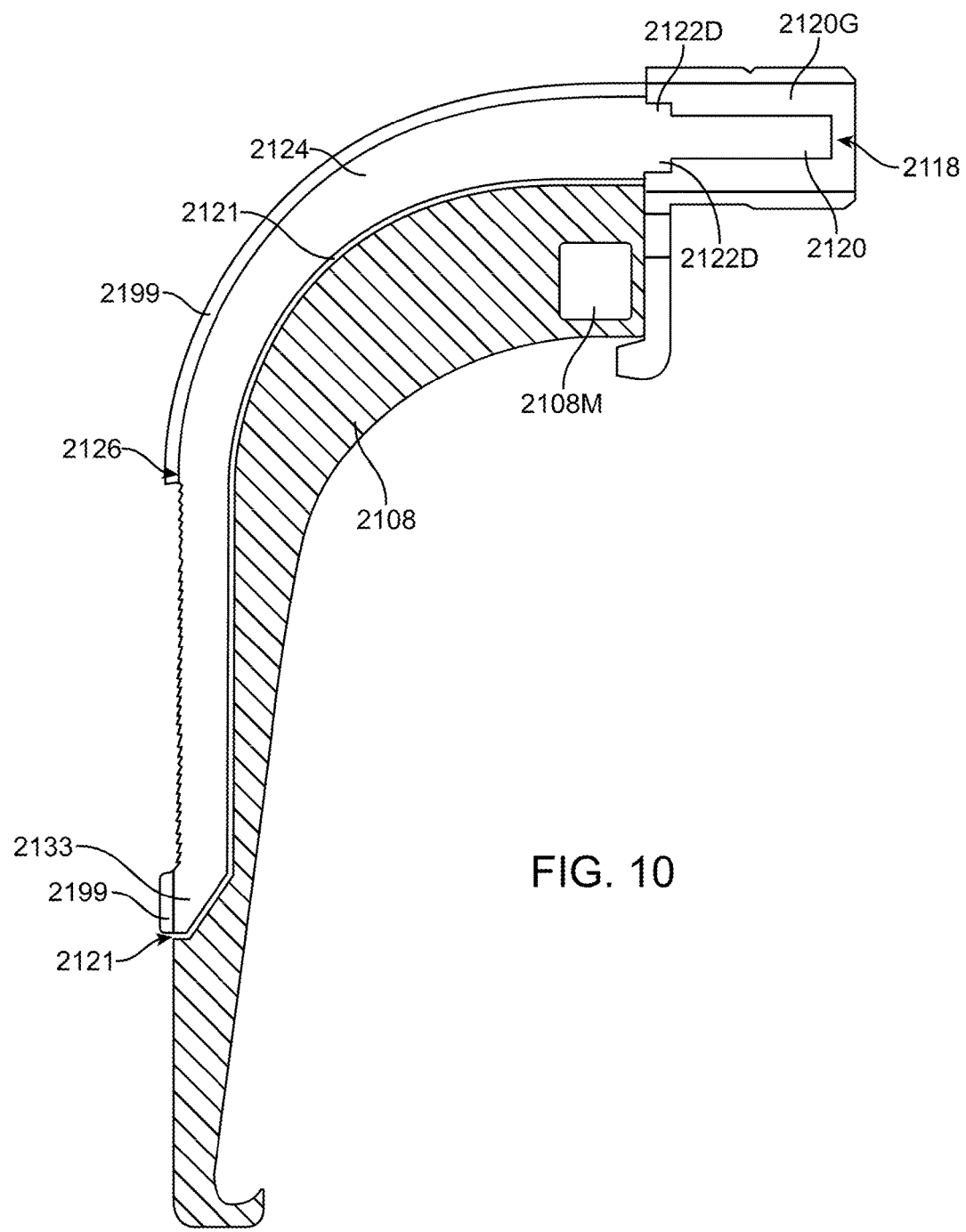
FIG. 10 is a partial cross-section view of the illuminated retractor of FIG. 9.

In the illustrated configuration illumination blade 2109 includes at least one dead zone, dead zone 2122D, generally surrounding input transition 2122. A dead zone typically comprises a portion of the waveguide where the light conducted by the waveguide inherently does not travel. The conducted light may not travel through a dead zone due to the geometry of the waveguide and the orientation/direction of the light being introduced to the waveguide. One or more dead zones at or near the output of the illumination blade provide locations for engagement elements such as tabs to permit stable engagement of the illumination blade to the retractor. This stable engagement supports the maintenance of an air gap such as air gap 2121 adjacent to all active zones of the illumination blade as illustrated in FIG. 10. Neck zone 2124 ends with dimension 2132 adjacent to output transition 126 which extends to dimension 134 at the output zones. The changing dimensions result in dead zones 2126D and 2126E adjacent to output transition 2126. These dead zones are suitable locations for mounting tabs 2114 to minimize any effects of the engagement elements on the light path. To minimize stresses on the light input and or stresses exerted by the light input on the illumination blade, the engagement elements are aligned to form an engagement axis such as engagement axis 2136 which is parallel to light input axis 2138.

Optionally (see also FIG. 10) surfaces of the illumination blade 2109 that are adjacent active zones are clad with a cladding layer that is configured to promote TIR. The cladding layer may also produce properties such as hydrophobicity or adhesiveness. Such cladding layers are described elsewhere in this disclosure. Surface areas of illumination blade 109 that are output zones remain unclad. The space occupied by air gap 2121 would instead by occupied by cladding layer 2199.

Output zones 2127, 2128, 2129, 2130 and 2131 have similar configurations with different dimensions. Referring to the detailed view of FIG. 11, the characteristics of output zone 2127 are illustrated. Each output zone is formed of parallel prism shapes with a primary surface or facet such a primary facet 2140 with a length 2140L and a secondary surface or facet such as secondary facet 2142 having a length 2142L. The facets are oriented relative to plane 2143 which is parallel to and maintained at a thickness or depth 2144 from rear surface 2145. In the illustrated configuration, all output zones have the same depth 2144 from the rear surface.

The primary facets of each output zone are formed at a primary angle 2146 from plane 2143. Secondary facets such as facet 2142 form a secondary angle 2147 relative to primary facets such as primary facet 2140. In the illustrated configuration, output zone 2127 has primary facet 2140 with a length 2140L of 0.45 mm at primary angle of 27° and secondary facet 2142 with a length 2142L of 0.23 mm at secondary angle 88°. Output zone 2128 has primary facet 2140 with a length 140L of 0.55 mm at primary angle of 26° and secondary facet 2142 with a length 2142L of 0.24 mm at secondary angle 66°. Output zone 2129 has primary facet 2140 with a length 2140L of 0.53 mm at primary angle of 20° and secondary facet 2142 with a length 2142L of 0.18 mm at secondary angle 72°. Output zone 130 has primary facet 2140 with a length 2140L of 0.55 mm at primary angle of 26° and secondary facet 2142 with a length 2142L of 0.24 mm at secondary angle 66°. Output zone 2131 has primary facet 2140 with a length 2140L of 0.54 mm at primary angle of 27° and secondary facet 2142 with a length 2142L of 0.24 mm at secondary angle 68°.

Figures 11, 12:
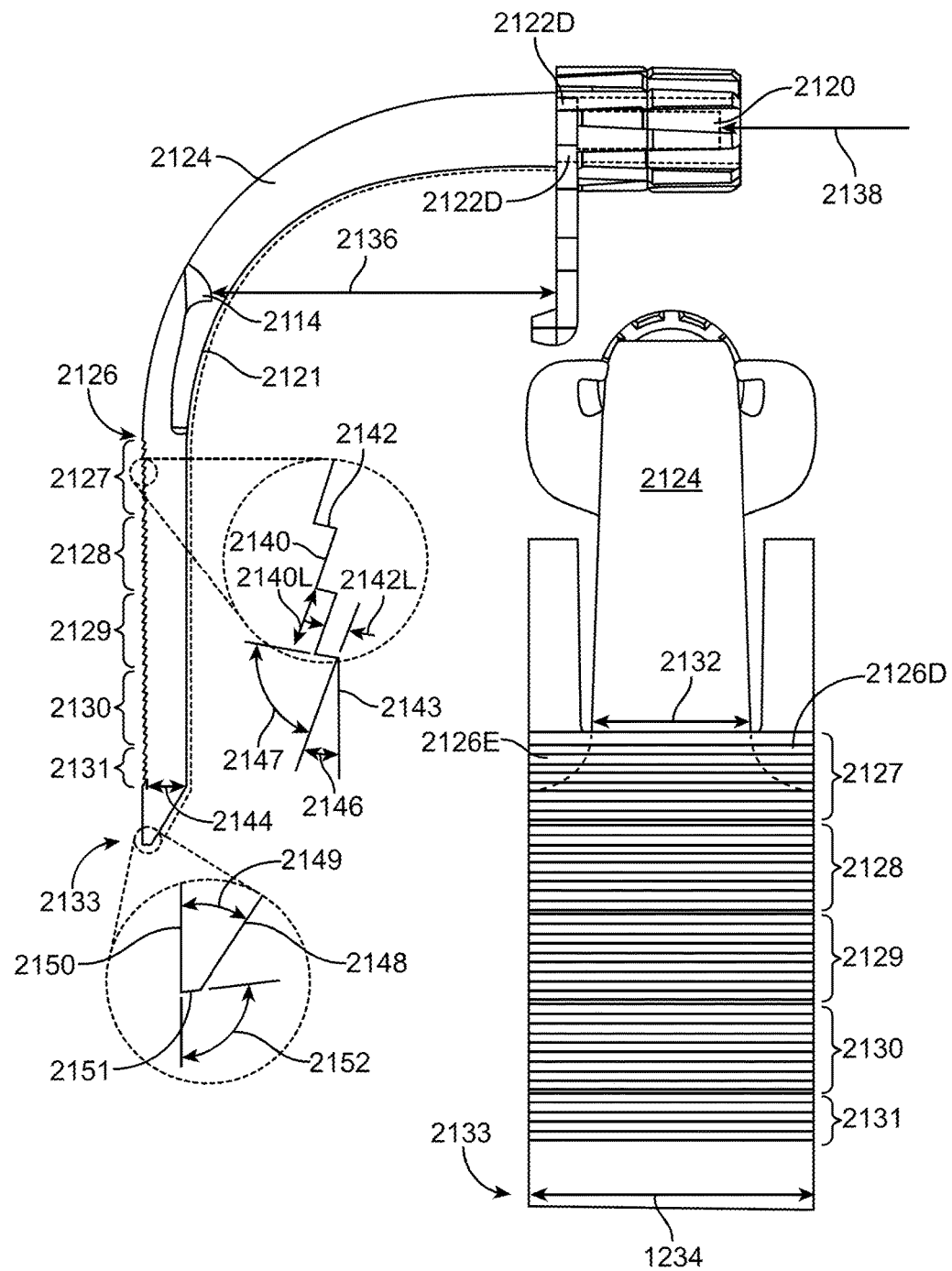
FIG. 11 is a side view of the illumination blade of FIG. 9.
FIG. 12 is a front view of the illumination blade of FIG. 9.

Output end 2133 is the final active zone in the illumination blade and is illustrated in detail in FIG. 11. Rear reflector 2148 forms angle 2149 relative to front surface 2150. Front surface 2150 is parallel to rear surface 2145. Terminal facet 2151 forms angle 2152 relative to front surface 2150. In the illustrated configuration, angle 2149 is 32° and angle 2152 is 95°.

Other suitable configurations of output structures may be adopted in one or more output zones. For example, output zones 2127 and 2128 might adopt a concave curve down and output zone 2129 might remain generally horizontal and output zones 2130 and 2131 might adopt a concave curve up. Alternatively, the plane at the inside of the output structures, plane 2143 might be a spherical section with a large radius of curvature. Plane 2143 may also adopt sinusoidal or other complex geometries. The geometries may be applied in both the horizontal and the vertical direction to form compound surfaces.

In other configurations, output zones may provide illumination at two or more levels throughout a surgical site. For example, output zones 2127 and 2128 might cooperate to illuminate a first surgical area and output zones 2129 and 2130 may cooperatively illuminate a second surgical area and output zone 2131 and output end 2133 may illuminate a third surgical area. This configuration eliminates the need to reorient the illumination elements during a surgical procedure.

Figure 13:
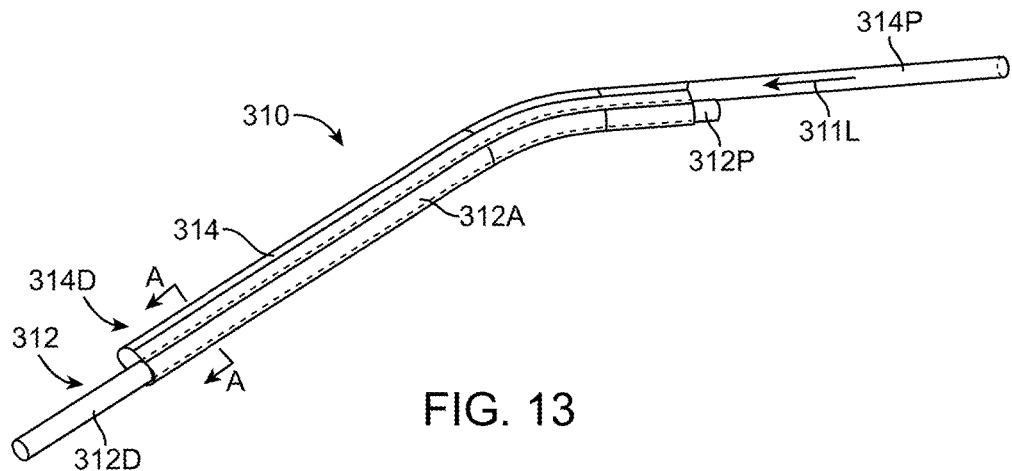
FIG. 13 is a perspective view of an illuminated suction apparatus.
Figure 13A:
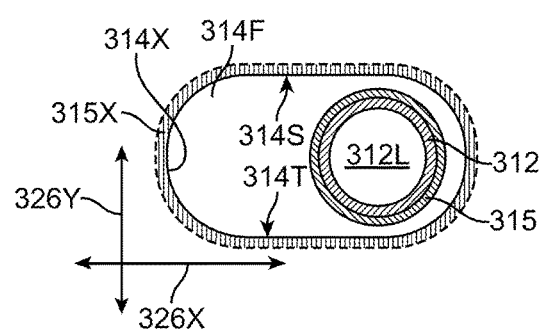
FIG. 13A is a cross-section view of the illuminated suction apparatus of FIG. 13 taken along A-A

Referring to FIGS. 13 and 13A, illuminated suction apparatus 310 includes suction tube 312 made of any suitable material such as aluminum, stainless steel or any suitable acrylic or other polymer. Suction tube 312 encloses suction lumen 312L. Illumination waveguide 314 is secured over cladding layer 315 on central portion 312A of suction tube 312 leaving input or proximal portion 312P and distal portion 312D exposed. Illumination waveguide 314 may have a flat side such as side 314S or side 314T to optimize light mixing as light 311L travels from illuminator input 314P to output 314D. Further details on illuminated suction apparatuses are provided in U.S. patent application Ser. No. 12/616,095 now U.S. Pat. No. 8,292,805, which is hereby incorporated by reference in its entirety.

Illumination waveguide 314 is made of an optical grade engineering thermoplastic such as cyclo olefin polymer which efficiently transmits light. Any other suitable material such as cyclo olefin copolymer, polycarbonate, acrylic and/ or TPC may also be used. The angles and bends of the waveguide structure are engineered so light transmits through the waveguide via TIR. The side walls and other features have angles and flat areas such that light is mixed and not allowed to escape until it reaches the distal end of the illuminator and exits with a selected uniformity. Light that is reflected by TIR is reflected with high efficiency (nearly 100% efficiency). Suction tube 312 introduces an interface with illumination waveguide 314 that will not be 100% reflective. Thus an uncoated or untreated suction tube will cause a small portion of light to be lost to absorption and or scattering at each reflection, ultimately resulting in poor light transmission efficiency. In order to preserve TIR through the waveguide, cladding material 315 with a specific index is placed between the suction tube and the waveguide. TIR can also be potentially disrupted by blood or foreign matter from the surgical site coming into contact with exterior exposed surface 314X of illumination waveguide 314. Exterior cladding layer 315X having a specific refractive index can also be attached to the outside of the waveguide. The waveguide material completely surrounds suction tube 312 in order to provide an illumination pattern from distal end 314D unobstructed by a shadow from the metallic suction tube. The waveguide and TIR-preserving materials are chosen to provide an optimized light exit angle, total light output, and illumination suited to properly visualize the surgical site. Suction tube 312 may be treated (for example anodized in the case of aluminum) in order to reduce glare or reflections resulting from interaction with light output from the illuminator.

Figure 14:
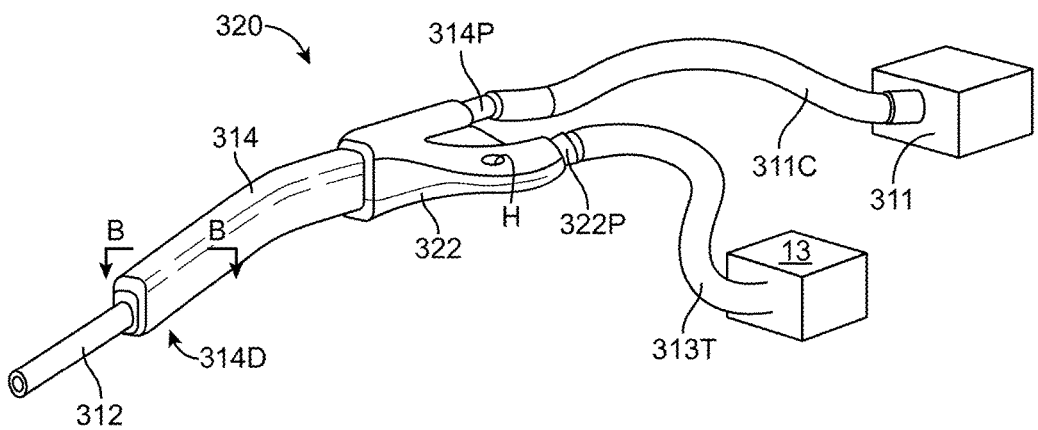
FIG. 14 is a perspective view of an illuminated suction apparatus with a handle.

Referring now to FIG. 14, light 311L from light source 311 is conducted to the illumination waveguide using any suitable apparatus such as fiber optic cable 311C and is then conducted through waveguide 314 and exits from any appropriate structure or structures on or near distal end 314D of the waveguide. Vacuum from suction source 313 is conducted to illuminated suction apparatus 319 using any suitable suction tube such as tube 313T which is connected to vacuum input 321P. The vacuum available at the distal end of suction tube 312 may be controlled by covering all or a portion of suction hole H in handle 321.

Illuminated suction apparatus 310 may be integrated into a handle such as handle 321 made of relatively low-cost engineering plastic such as ABS or polycarbonate. Handle 321 may be formed from two or more components that could be separately injection molded components designed to be snap fit, glued, or ultrasonically welded together. Alternatively, the handle could be formed over an illuminated suction apparatus such as apparatus 310 through an overmolding process. The proximal portion of the combined device such as illuminated suction apparatus 319 would also contain a hole, hole H, properly positioned to allow the surgeon to enable the suction function by obstructing all or a portion of the hole with a finger; the hole communicates with the suction pathway in the device, disabling suction by creating a "suction leak" when it is not blocked. Varying the hole geometry, as in the case of Fukijima suction, affords finer modulation of the suction function. The proximal end of handle 321 may also contain inputs for a traditional fiber optic cable to be attached to illumination waveguide 314, such as a male ACMI connection or other suitable connector, and a vacuum port such as vacuum port 321P which may be a barbed fitting suitable for standard flexible suction PVC suction tubing of various sizes to be attached. The fiber optic cable is attached to a high-intensity light source such as light 311. Suction tube 313T is attached to any standard vacuum source in the operating room (OR) such as a waste collection container with integrated vacuum pump such as vacuum source 313.

Figure 15:
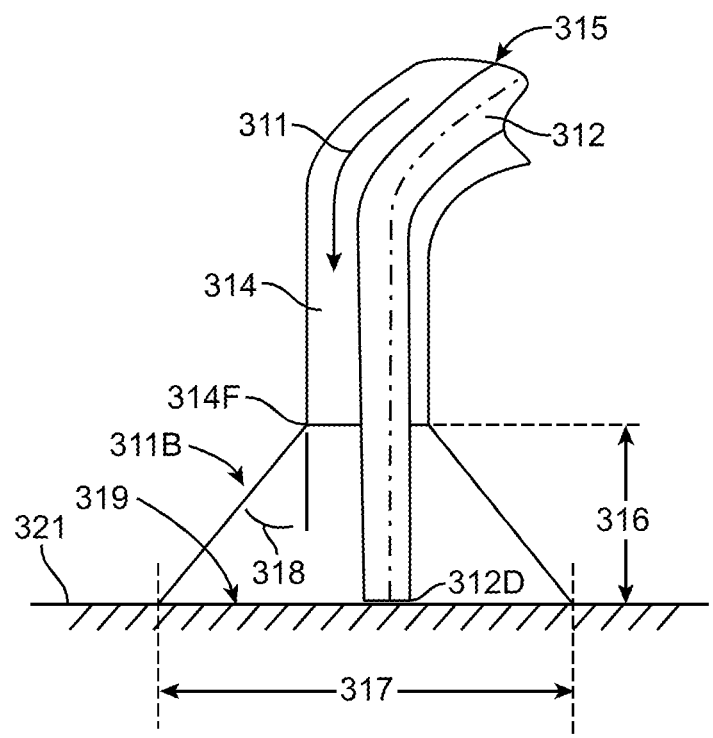
FIG. 15 is a cross section view of the distal end of the illuminated suction apparatus of FIG. 14 taken along B-B.

Referring now to FIG. 15, light beam 311B exits waveguide distal face 314F at a specific angle based on the optical properties such as the numerical aperture (NA) of the input source, index of refraction of the material, and shape of the waveguide. Light pattern 319 cast onto the target surgical field is optimized based on the specific distance 316 the illuminator is set back from the distal tip 312D of the suction tube. For a given light source configuration, divergence angle 318 of light beam 311B results in a specific illumination pattern 319 with a total light output and illumination size 317 at any target plane normal to the illuminator such as plane 321. The plane at the distal tip of the suction tube is of particular interest, since the physician will place the distal tip at the desired surgical target to enable suction or retract tissue.

Figure 15A:
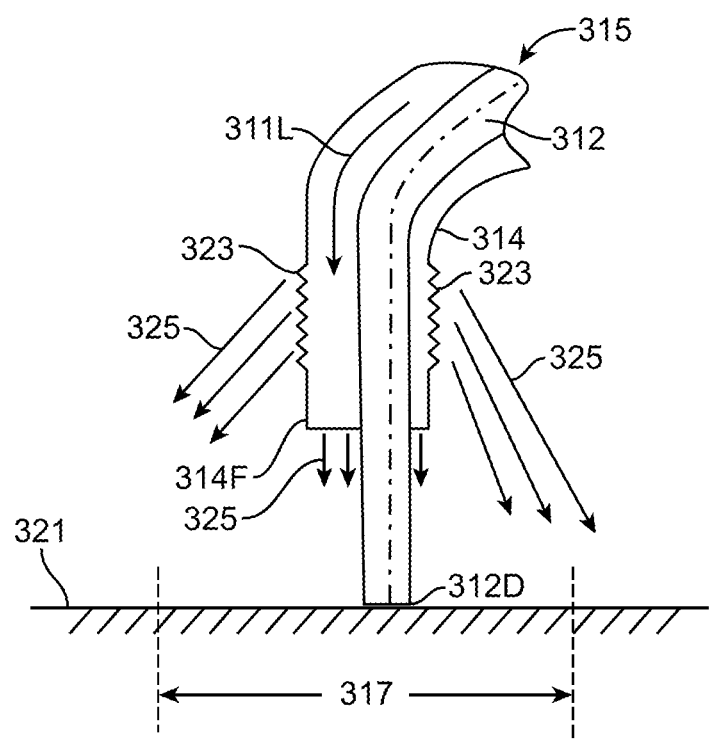
FIG. 15A illustrates an exemplary embodiment of light extraction from a lateral surface of the illuminated suction apparatus.

FIG. 15A illustrates an alternative embodiment of an illuminated suction apparatus having light extraction features 323 on a lateral surface of the illumination waveguide that extract light 325 and direct the light 325 laterally and distally toward the surgical field. This may feature may be used alone or in combination with the distal features previously described above. The extraction features may include prisms, lenses, lenslets, multiple facets, or other surface features known in the art that extract light from the waveguide and direct the light to a desired area in a desired pattern. The extraction features may be disposed in a discrete area to extract light only from that area, or the extraction features may be disposed circumferentially around the waveguide so that a uniform ring of light emits from the waveguide. Using both lateral extraction features and distal light features allows diffuse light to emit from the lateral surfaces of the waveguide while more focused light can be emitted from the distal tip of the waveguide.

Figure 16:
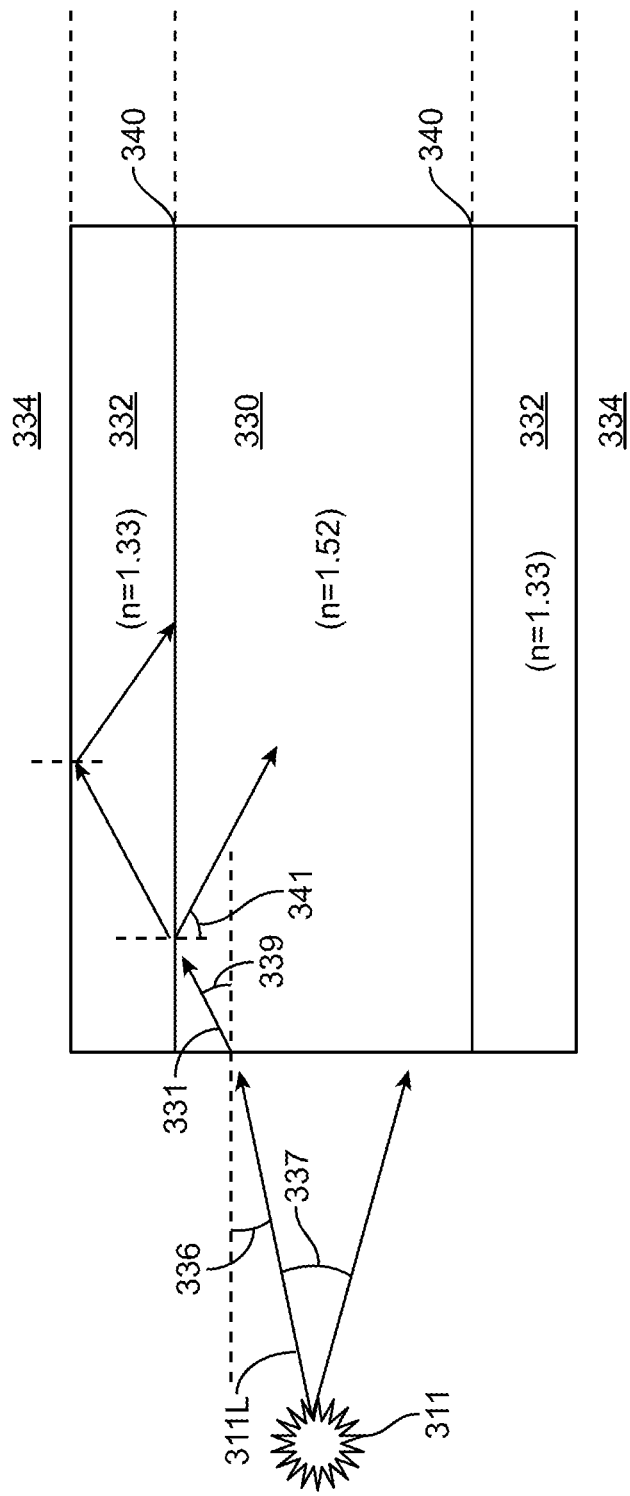
FIG. 16 is a cross section view of an illumination conduit input.

Referring now to FIG. 16, light source 311 is transmitting light 311L into cyclo olefin polymer core 330 with refractive index 1.52, fluorinated ethylene propylene (FEP) cladding 332 with refractive index 1.33, and an external environment 334 surrounding cladding 332. Light source 311 is assumed to be in air with a refractive index of 1.0 and a numerical aperture (NA) of 0.55 which corresponds to a half-cone angle, angle 336, of 33.4 degrees. The NA of source 311 is the angle of incidence on the core when light 311L is coupled in which corresponds to angle 337. Internal light rays 331 initially enter core 330 at the half cone angle of 33.4 degrees and are refracted at an angle of 21.2 degrees, with internal refraction angle 339 when they pass into core 330. Internal light 331 then intersects core-cladding boundary 340 at an angle of 68.8 degrees which is angle 341. As long as angle 340 is greater than the critical angle determined by the core and cladding indexes, light 331 will undergo TIR and none of light 331 will be transmitted into the cladding. In this case (n-core=1.52 & n-cladding=1.33) the critical angle is 61.0 degrees.

This ray trace can be worked backwards from the critical angle to determine the maximum source NA that will still allow for all light to undergo TIR at the core-cladding boundary. If reflection angle 341 is 61.0 degrees which corresponds to the critical angle for the selected core and cladding, then internal refraction angle 339 is 29 degrees which means that angle 337 must be 47.4 degrees. From 47.4 degrees, the source NA is calculated to be 0.74. Therefore, when using the cyclo olefin polymer/FEP combination, an input source with a much higher NA/Efficiency can be used.

As described elsewhere in this disclosure the cladding materials may optionally or further comprise one or more of the following materials: fluoro polymers such as fluoro acrylate, a fluoro methylacrylate, or polytetrafluoroethylene (PTFE).

If the source NA is such that all the light coupled into the waveguide undergoes TIR at the core-cladding boundary, then no light is propagating in the cladding and the environment index does not affect the waveguide transmission and no light is hitting the cladding-environment boundary. The data in Table 1 below shows how the critical angle changes at the core-cladding boundary as the cladding index changes from 1.0 to 1.46 for a cyclo olefin polymer core (n=1.52). This is particularly relevant when designing refractive structures. Knowing the critical angle ahead of time, based on the environment or cladding, the structures can be designed to preferentially leak light from the illumination conduit.

TABLE 1

| Cladding Index | Core-Cladding Critical Angle (degrees) |
| --- | --- |
| 1.00 | 41.1 |
| 1.10 | 46.4 |
| 1.20 | 52.1 |
| 1.30 | 58.8 |
| 1.40 | 67.1 |
| 1.417 | 68.8 |
| 1.42 | 69.1 |
| 1.44 | 71.3 |
| 1.46 | 73.8 |

Any suitable cladding materials such as FEP can be applied to central portion 312A of suction tube 312 through methods such as manual or semi-automated shrink application of oversized FEP with a heat gun or focused heat from a hot-box nozzle, leveraging FEP's characteristic shrink ratio. Any other technique of a cladding such as FEP may be used such as applying a liquid coating or vapor deposition of FEP to central portion 312A or any other suitable surface to be clad. Suction tube 312 with integrated cladding 315 can then have illumination waveguide 314 insert-molded (via conventional high-volume injection molding) and waveguide 314 will be able to maintain total internal reflection. Use of cladding 315 between suction tube 312 and illumination waveguide 314 enables the suction tube to be formed of any suitable material such as metal or plastic. The choice of the plastic material for the suction tube needs to be such that the index of that material is below 1.42 for use with a waveguide having an index of 1.52 to maintain the differential at the interface of the suction tube and the waveguide. However, use of plastic may create challenges with injection molding processes which require relatively high temperatures and pressures inside of the molding cavity. Alternatively the device can be manufactured such that illumination waveguide 314 is formed with an internal lumen with no additional suction conduit running through it. The challenge posed by this approach is the potential light transmission efficiency losses stemming from evacuating biological material (blood, etc) through the lumen and making contact with the internal surface of the illumination waveguide lumen throughout the procedure.

Cladding with an index of 1.33 shows no light transmission dependence on the refractive index of the surrounding environment or the cladding thickness when used with an illumination waveguide having a refractive index at or near 1.52. For a cladding with an index of 1.33, the light coupled into the illumination waveguide is constrained to the core due to total internal reflection at the core-cladding interface. Thus, there is no light propagating through the cladding, making the cladding-environment boundary condition a negligible factor in transmission. Teflon FEP with an index of 1.33 used as a cladding material with a cyclo olefin polymer core with index 1.52, shows no dependence on cladding thickness in three representative simulated surgical environments.

While preferred embodiments use heat shrink as the cladding over the suction tube and/or over the waveguide, optionally, a low index of refraction polymer may be injection molded or otherwise formed over the waveguide. This allows the polymer to minimize light loss from the waveguide, and also allows the polymer casing to be used for attaching to the suction tube or other surgical instruments. For example, the two may be bonded together, solvent bonded, welded, or otherwise joined together. In still other embodiments, snaps or other coupling mechanisms may be joined to the polymer and suction tube forming a snap fitting.

An illumination waveguide formed from material with a refractive index of 1.46, showed light transmission dependence on both cladding thickness as well as the external environment. This is a result of introducing light into the illumination waveguide at an NA of 0.55. Under this condition, light enters the core at an angle that is less than the critical angle of the core-cladding boundary, resulting in light propagating into the cladding. Since light propagates through the cladding, the cladding-environment boundary condition (critical angle) is a factor in the light transmission. Due to light propagating through the cladding, the cladding thickness also affects the transmission, because as the thickness increases, the rays bounce at the boundaries fewer times as they traverse the length of the waveguide.

Straight waveguide geometry in which the light traversing the structure encounters no bends or radii results in the greatest optical efficiency. However, due to ergonomic constraints or compatibility and management of essential accessories related to the device such as proximally attached fiber optic cables and suction tubing, it may be advantageous to design the proximal light input such that it creates an angle relative to the distal transmission body of the waveguide structure.

Figure 17:
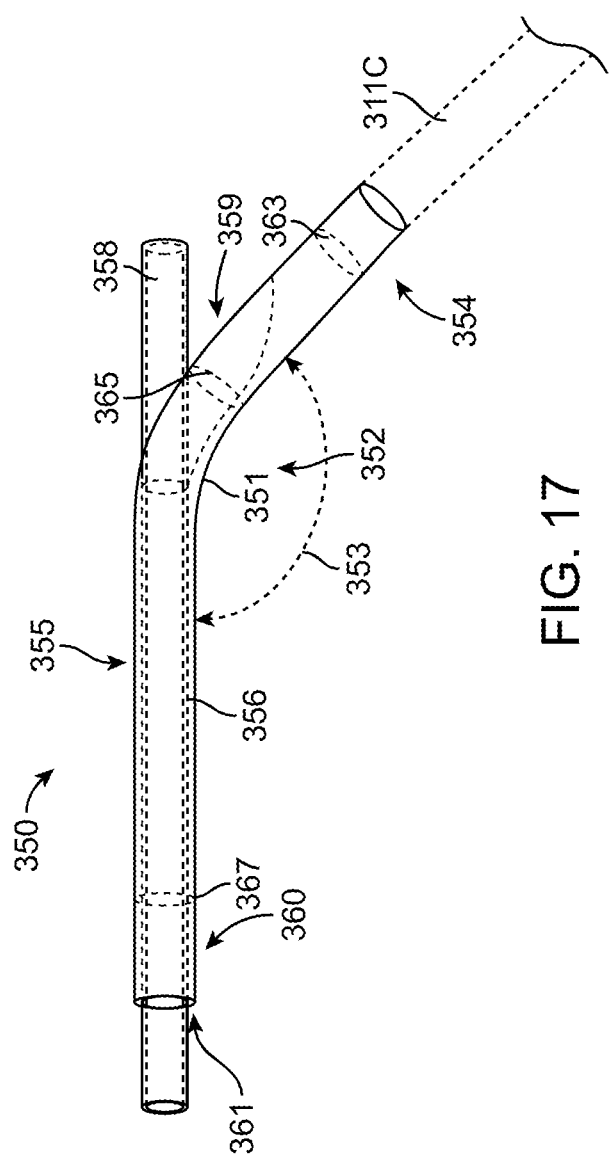
FIG. 17 is a side view of an alternate illumination conduit.
Figure 17A:
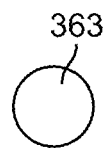
FIGS. 17A, 17B and 17C are various cross-section views of FIG. 17.

Referring now to FIGS. 17 and 17A, to preserve TIR and maximize transmission efficiency in illuminated waveguide 351 of suction apparatus 350, central portion 352 between light input section 354 and illuminated waveguide body 355 may be curved to form angle 353 between the input and body as close to 180 degrees as possible. Almost any bend or radius in the tube will cause some light leakage. However, if angle 353 in central portion 352 is limited to 150 degrees or greater, the light leakage is very low and the light transmission efficiency is maximized. Where angle 353 is less than 150 degrees, light leakage may be reduced by reducing or otherwise controlling the divergence of the light within the waveguide or by using any other suitable technique.

The shape of illuminated waveguide 351 morphs or cylindrically "sweeps" or "blends" from a solid cylindrical input, input section 354 into a circular hollow tube of waveguide body 355. Waveguide bore 356 may accommodate any suitable surgical tools such as suction tube 358. Suitable surgical tools access waveguide bore 356 through access opening 359. As discussed above, light exits waveguide body at or near distal end 360 with the majority of light exiting through distal surface 361. Distal surface 361 may be flat or it may any other suitable simple or complex shape. Distal surface 361 may have any of the surface features disclosed herein for extracting and directing light to a field of illumination.

Figure 17B:
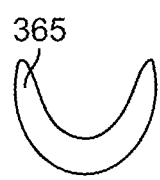
Figure 17D:
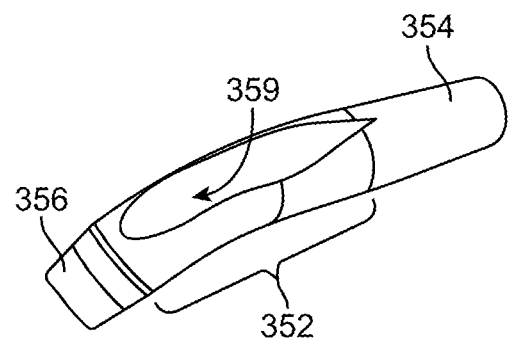
FIG. 17D is a perspective view of access port of the alternate illumination conduit of FIG. 17.
Figure 17C:
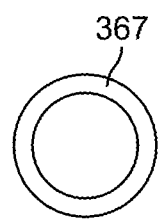
Figure 17E:
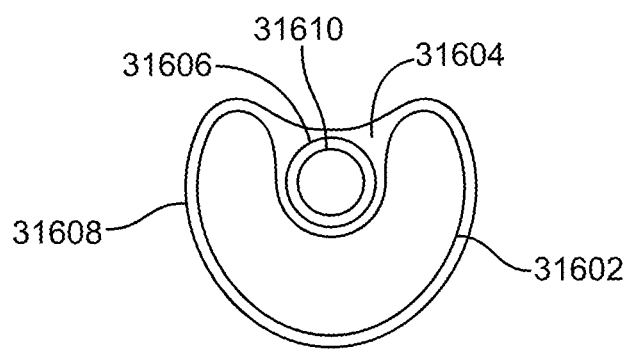
FIG. 17E illustrates an exemplary cross section of an illumination conduit.

As the cross sectional area of illuminated waveguide 351 increases along the light transmission path from section 363 of input section 354 to central section 365, to distal cross-section 367 near distal end 360, the NA of the illumination waveguide increases, thus increasing the light divergence as light emerges from the distal end of the illuminator. The NA can also be influenced by bends. It may be possible to counter-bend to adjust the NA. Other techniques for controlling the NA of the waveguide may also include molding or machining features into the surfaces of the waveguide. The concepts illustrated above can also be manufactured as two halves that are over molded around any suitable surgical tool such as suction tube 58. FIGS. 17A-17C illustrate various cross-sections of the waveguide in FIG. 17, and FIG. 17D highlights the area surrounding opening 359. Thus, in the FIG. 17B, a suction tube 31610 is disposed in the concave saddle portion 31604 of the waveguide 31602 as seen in FIG. 17E. Optical cladding 31606 such as heat shrink tubing (or fluoropolymer and the like) is disposed circumferentially entirely around the suction tube 31610, and then another layer of optical cladding 31608 such as heat shrink (or fluoropolymer and the like) is disposed entirely around the circumference of both waveguide 31602 and suction tube 31610. A portion of the cladding on the suction tube contacts a portion of the outer cladding where no waveguide surrounds the suction tube. Additionally, in this embodiment, the inner saddle has a first radius of curvature and the outer surface has a different radius of curvature (here larger than the inner radius of curvature). Alternative embodiments may have other combinations of radii of curvature.

Figure 18:
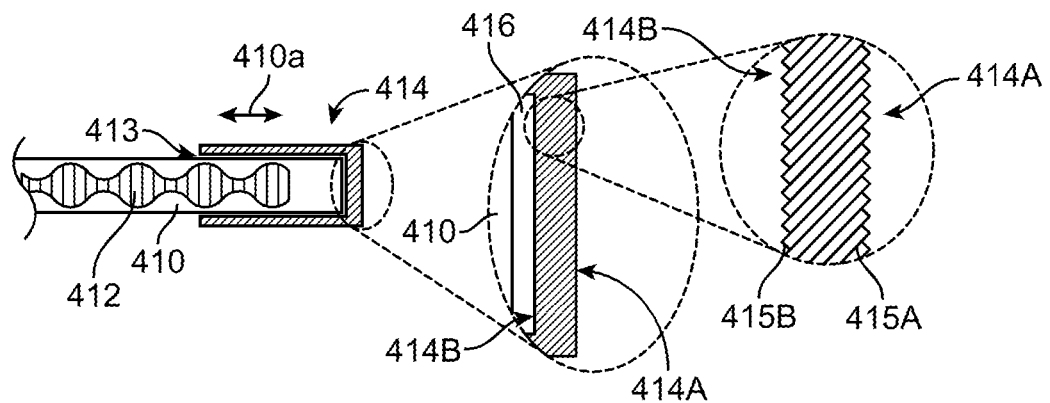
FIG. 18 is a cutaway view of a fiber and micro structure optical end cap.

In FIG. 18 medical illumination fiber 410 engages an end cap such as cap 414 to form an optical path with one or more micro structure optical surfaces such as inner optical surface 414A or outer optical surface 414B and or one or more air gaps such as gap 416 and or index matching material to control light 412. Any suitable surface such as inner and outer optical surfaces 414A and 414B or a portion of an inner or outer surface may be formed to include micro structure optical structures such as structure 418A and or 418B thereon. Cap 414 may be made of glass, plastic or any other suitable material and may be sized to enable bore 413 to frictionally engage optical fiber 410. Optionally, the sides of cap 414 may comprise a cladding layer 4199 configured to both promote TIR and frictionally engage fiber 410.

Input and or output micro optical structures such as structure 418A or structure 418B may adopt any suitable configuration to accomplish one or more of the functions of diffracting, deflecting, refracting or polarizing light passing through the micro structure optical component. Such structures individually or in combination may be used to adjust the intensity and or the phase of the light energy similar to holographic film which may also be used.

Figure 19:
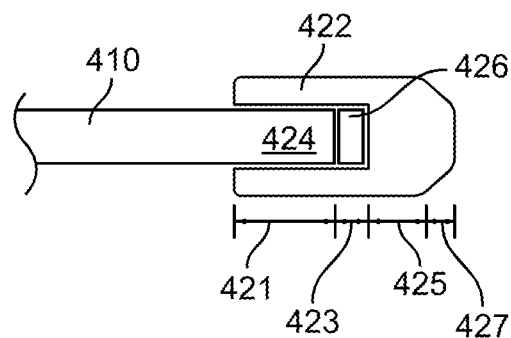
FIG. 19 is a cutaway view of a micro structure optical end cap.

Referring now to FIG. 19 illumination fiber 410 includes a light management cap such as cap 422 engaging end 424 of fiber 410. A light management cap according to the present disclosure such as cap 422 may engage a fiber along engagement zone 421 mechanically, frictionally, or using adhesives or any other suitable technique. Matching zone 423 of cap 422 may be an air gap, or be filled with any suitable material such as adapter material 426 to achieve a suitable index transition between illumination fiber 410 and cap 422. Body zone 425 of cap 422 may be composed of solid cap material, or any suitable combination of air gaps or inserted components may also be used. Cap zone or output zone 427 may be formed in any suitable shape and may include microstructure such as structures 418A and 418B to achieve desired output light management.

Figure 20:
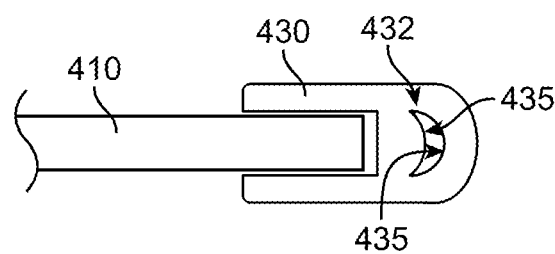
FIG. 20 is a cutaway view of a micro structure optical end cap.

Referring to FIG. 20, light management cap 430 may include one or more chambers or other inserted structures to control light emanating from illumination fiber 410. Chamber 432 may be filled with air or other suitable material to achieve the desired light management. Incident surface 433 and outlet surface 435 of chamber 432 may be formed to have any suitable surface characteristics such as surfaces 418A and 418B.

Figure 21:
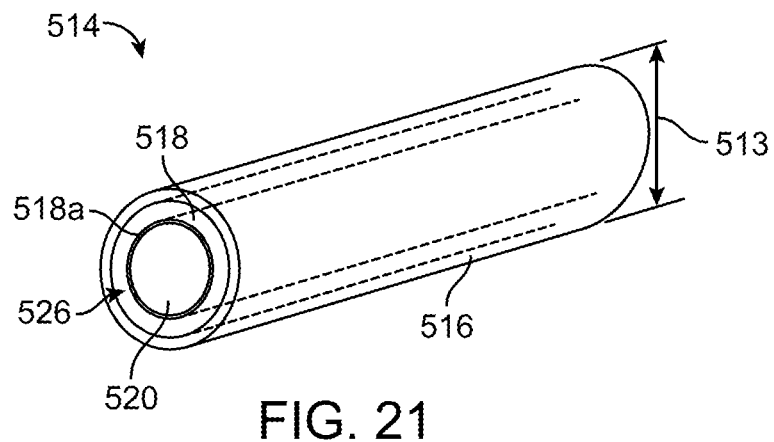
FIG. 21 is a perspective view of the distal end of an endoscope with an optical waveguide sheath.

Provided herein are embodiments directed to cladded optical waveguide cannula systems. Further details of optical waveguide cannula (sometimes referred to as sheath) systems may be found in U.S. patent application Ser. Nos. 11/715,247 and 12/412,764 now U.S. Pat. Nos. 7,901,353 and 8,162,824, respectively, the entire contents of both of which are hereby incorporated by reference. Referring now to FIG. 21, optical waveguide system 514 may accommodate any suitable surgical instrument such as for example, a drill, burr or endoscope 518 which is encased, enclosed or otherwise surrounded by optical waveguide sheath 516. An optical waveguide sheath is a generally annular or cylindrical shaped structure and may be manufactured separately and may be a single use device. In the event of a failure of an optical waveguide such as optical waveguide sheath 516, a replacement may be introduced immediately. One or more flow paths such as flow path 526 may be created between endoscope 518 and optical waveguide sheath 516. Flow path 526 may be used for any suitable service such as suction, irrigation, ventilation or the introduction of other tools or devices. A waveguide sheath may be subjected to forces during use, such as a prying force, that may weaken or break it. Structural elements such as gussets or ribs may be added to waveguide sheath 516 in the bore between the sheath and endoscope 518 that serve to strengthen waveguide sheath 516. A film may be added to the outside of waveguide sheath 516 to secure pieces that may become broken during use to prevent the broken pieces from dropping into the surgical work space. Said film may serve an optical function as well, e.g., enhancing total internal reflection within the wall of waveguide sheath 516. Optionally, cladding layer 5199 may be applied to the surface of sheath 516 to enhance TIR Surgical devices such as endoscope 518 may be made without an illumination element and thus aperture 520 may be increased without increasing overall dimension 513. Wall 518A of endoscope 518 may also perform as an optical waveguide to improve illumination and may provide an alternate light path to enable illumination of different characteristics.

Figure 22:
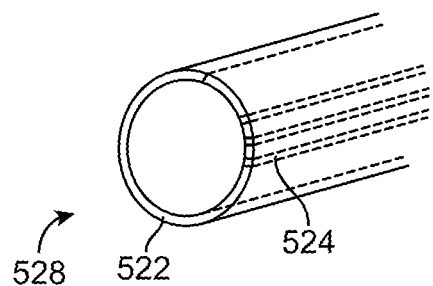
FIG. 22 is a perspective view of the distal end of an optical waveguide sheath.

Referring now to FIG. 22, waveguide sheath 528 may be a single generally uniform element, it may be composed of two or more distinct illumination pathways forming an apparently singular conduit, or it may be composed of one or more parallel light conducting elements such as light path element 524 or light path element 592 of FIG. 14. Cladding layer 5199 may be applied to sheath 528 or each light conducting element therein to enhance TIR. Moving the illumination element from conventional endoscopes to a separate device such as a light conduit such as waveguide sheath 528 permits illumination surface 522 to be larger than many conventional illumination elements. Surrounding an apparatus such as an endoscope with the optical waveguide may provide generally uniform illumination for any orientation of the endoscope or other device.

Figure 23:
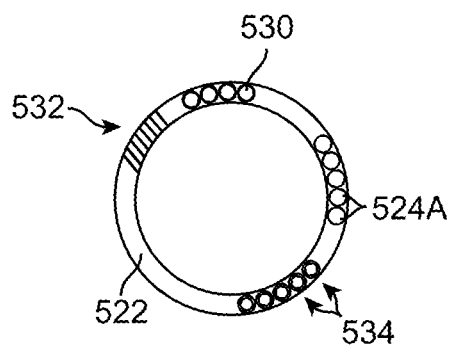
FIG. 23 is an end view of the distal end of an optical waveguide sheath.

Referring now to FIG. 23, illumination surface 522 may adopt any suitable configuration to provide illumination. For example facets such as facets 530 may direct light energy in any selected direction and may be coated or otherwise treated to introduce filtering for frequency and/or polarization. Microstructures such as microstructures 532 may be used to achieve directed light energy, filtering or other. One or more lens structures may be coupled to illumination surface 522, or they may be formed in or on illumination surface such as lenses 534. Alternatively, these elements may also be combined.

Using separate light conducting elements such as light path elements 524 may permit selective illumination through a waveguide sheath as well as provide multiple illumination paths for illumination having different characteristics such as polarization, wavelength or intensity. Each light path element may include microstructures, facets, lenses or other suitable treatment on distal face 524A. At least a portion of light path elements 524 may be cladded with cladding layer 5199 to enhance TIR.

Figure 24:
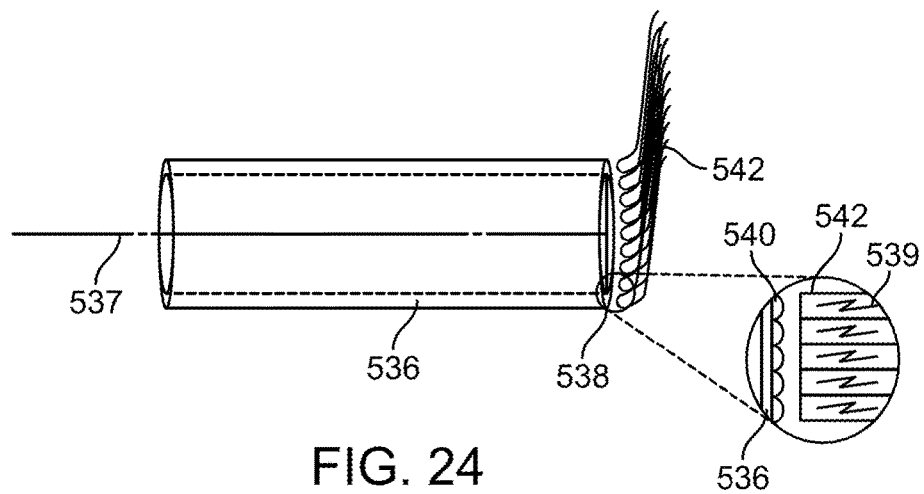
FIG. 24 is a side view of an optical waveguide sheath coupling to fiber optic elements.
Figure 25:
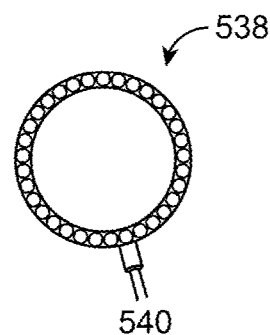
FIG. 25 is an end view of the fiber optic coupling lens array of FIG. 24.

In FIGS. 24 and 25 coupling ring 538 is provided to couple light from fibers 542 into optical waveguide 536. Optional cladding layer 5199 is shown applied to waveguide 536, the cladding layer 5199 may cover at least a portion of the waveguide's 536 internal (not shown) or external surface. Coupling ring 538 permits rotation of optical waveguide 536 about bore centerline 537 without rotating fibers 542. Coupling ring 538 may be made reusable since it includes the expensive optical fibers whereas optical waveguide 536 may be made disposable, e.g., as an inexpensive plastic injection molded part using a suitable optical material such as acrylic or polycarbonate. Coupling ring 538 may also include any suitable light coupling structure such as coupling lenses such as lenses 540, each lens coupling light energy 539 from a fiber 542 into optical waveguide 536. The lenses or suitable microstructure may be spherical, cylindrical or aspherical or non-symmetrical depending on the light source. In the case of fiber optics, a spherical lens may be used to match the numerical apertures (acceptance angle) of the fiber optic and the optical waveguide. Because a specific cone angle of light exits a fiber optic cable, a matching acceptance angle should be used for the coupling ring.

Figure 26:
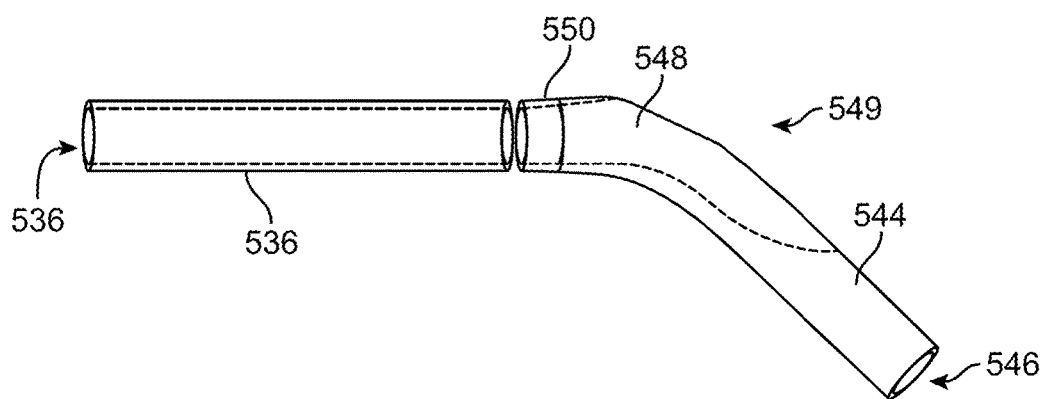
FIG. 26 is a side view of an optical waveguide sheath with a light-coupling adapter.
Figure 27:
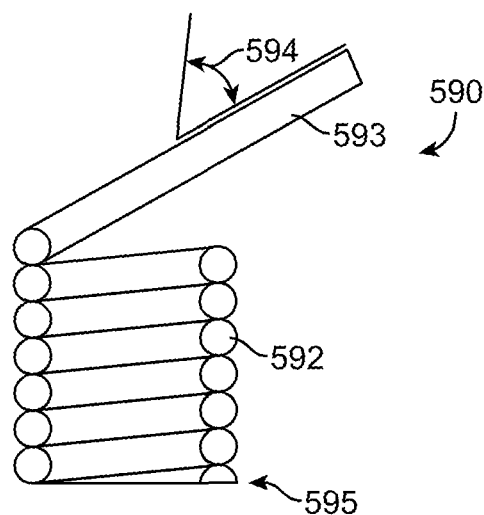
FIG. 27 is a cutaway view of an optical waveguide.
Figure 27A:
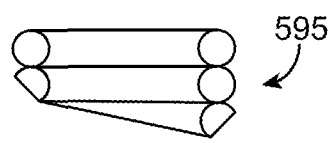
FIGS. 27A-27D are cutaway views of distal ends of the optical waveguide of FIG. 27.
Figure 27B:
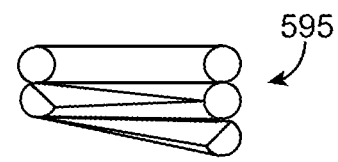
Figure 27C:
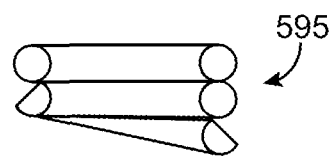
Figure 27D:
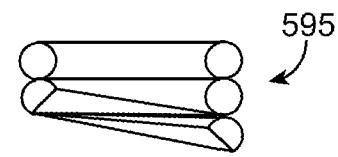

Referring now to FIG. 26, light coupling adapter 544 may be used to couple light energy in through face 546 and directs the light energy around access channel 548 and through adapter ring 550 into optical waveguide 536. The coupling adapter may also comprise cladding layer on at least a portion of its external or internal surface (not shown) for enhancing TIR. Access port 549 and access channel 548 provide access to bore 535 for any suitable surgical tool, apparatus or device. Adapter ring 550 engages waveguide 36 while permitting relative motion of waveguide 536 relative to light coupling adapter 544. Alternatively, coupling adapter 544, adapter ring 550 and optical waveguide 536 may be contiguous with no relative motion permitted. Coupling ring 550 may also be an element of waveguide 536 as well as an element of light coupling adapter 544.

Alternatively, optical waveguide 590 as illustrated in FIGS. 27 and 27A-27D may be formed using one or more solid light guides such as light path element or rod 592 and forming the one or more rods into a spring like spiral. Input 93 may be formed at any suitable angle 594 with an optimal angle between 45° and 90°. Distal end 595 may be cut or formed to have any suitable configuration to reflect or emit light in any suitable direction or directions as illustrated in FIGS. 27 and 27A-27D for example. A spiral waveguide may be mechanically flexible, much as a spring is flexible. The spiral waveguide may be part of an assembly that includes rigid or semi-rigid tubular waveguides interconnected by spiral waveguides. Either or both of the tubular and spiral waveguides may have light extraction structures.

Referring now to FIGS. 28-31, light input connector 5152C surrounds light input cylinder 5152 which may be divided into multiple input arms such as arms 5151 and 5153 that then direct light into illumination waveguide 5150. Input arms 5151 and 5153 may assume any suitable shape and cross-sections depending on the optical design goals, such as the multi-radius arms with rectangular cross-section shown or straight sections (no radius) or angle rotators, etc. Also shown is a clamp flange holder 5159 that serves to support input connector 5152C and arms as well as providing a standard light connector 5152C over input cylinder 5152 (e.g., an ACMI or Wolf connector) and a flange 5159F at the top for attaching a clamp used to hold the entire structure in place once it is positioned relative to a surgical site in a body. A shelf or other similar light blocking structures may be added to the holder, extending over the input arms and or the upper tube edge as needed to help block any light that may escape these structures that might shine up into the user's eyes. Circumferential light extraction structures 5154 are shown at the bottom, distal end 5156, of the tube. In the section view of FIG. 29, vertical light disruption structures or facets 83F are shown on the inside wall of the tube.

Figures 28, 29:
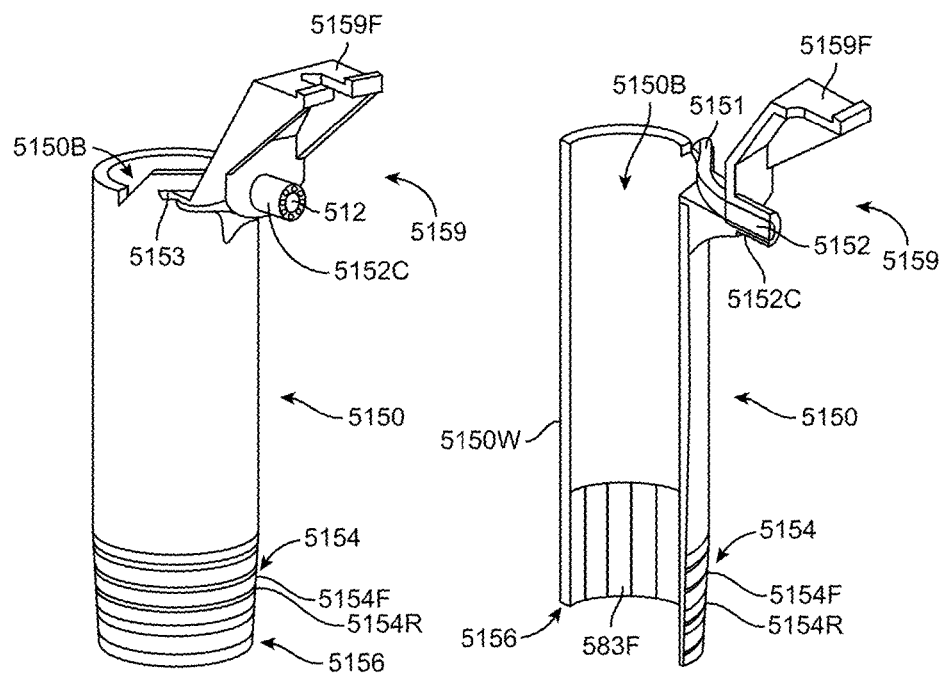
FIG. 28 is a perspective view of an optical waveguide with a reinforced and shielded split input coupling.
FIG. 29 is a cutaway view of the optical waveguide of FIG. 28.
Figure 30:
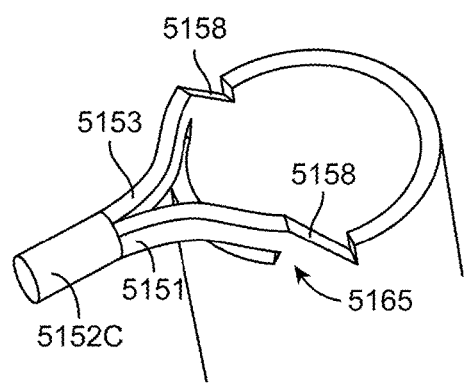
FIG. 30 is a cutaway view of the optical waveguide of FIG. 28.
Figure 31:
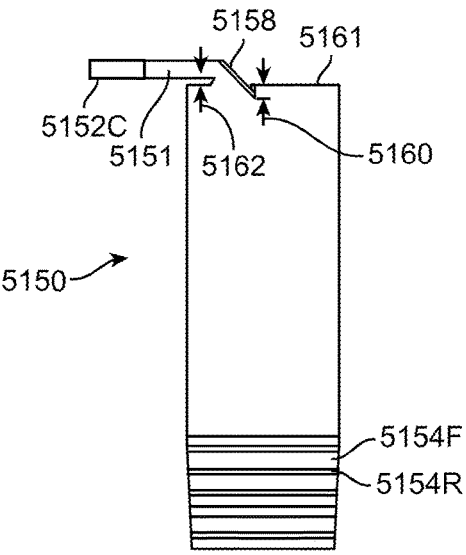
FIG. 31 is a side view of the optical waveguide of FIG. 30.
Figure 32:
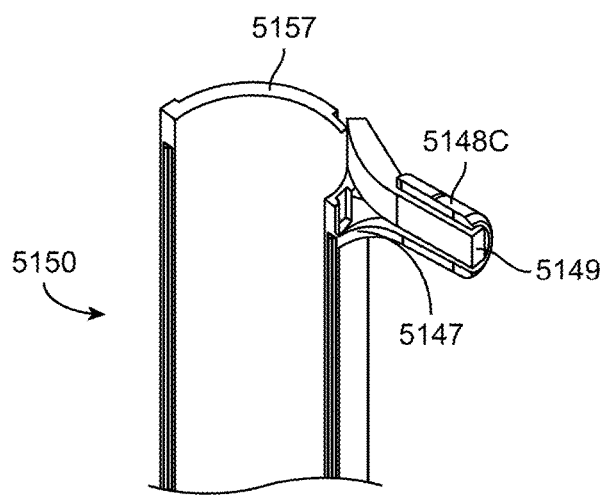
FIG. 32 is a cutaway view of an optical waveguide with the clamp assembly removed for clarity.

Illuminated cannula 5150 of FIG. 28 includes clamp adapter 5159F that also support light coupling 5152C for introducing light energy into cannula 5150. The relative orientation of the clamp adapter and the light coupling as shown enables the clamp adapter to operate as a shield to prevent any misdirected light shining into the eyes of anyone looking into bore 5150B of the cannula, but the clamp adapter and light coupling may adopt any suitable orientation.

FIG. 29 illustrates vertical facets 583F within the distal end for disrupting the light spiraling within the waveguide. Circumferential light extraction structures 5154 may include stepped facets such as facets 5154F and risers such as riser 5154R on the outside tube wall 5150W. The "riser" section of the stepped facet section 154R is angled so that it may slide against tissue without damaging the tissue. Steps may be uniform or non-uniform depending on the light directional control desired. The steps may be designed to directly light substantially inwards and toward the bottom of the tube or some distance from the bottom of the tube, or they may be designed to direct light toward the outside of the tube, or both.

Circumferential light extraction structures such as structures 5154 may be facets or may be other geometries, such as parabolas. Circumferential light extraction structures coupled with light directing structures that provide circumferentially distributed light to the extraction structures provide circumferential illumination. Since tools entering the interior of the tube now have light shining on them from all sides, the tools do not cast any shadows within the cone of illumination emitted by the cannula. The circumferential illumination from a cylindrical waveguide creates a generally uniform cone of light that minimizes shadows, e.g., from instruments, creating substantially shadowless illumination in the surgical field below the tubular waveguide.

Cannula 5150 of FIGS. 30-33 is illustrated without clamp flange/holder 5159 in place. Input arms 5151 and 5153 are offset above proximal surface 5161 by a distance 5162 and end in angled reflector surface 5158 that partially extends down distance 5160 into the tube wall. The offset controls the light entering waveguide 5150 and restricts light entering to input structure 5165. Reflector surface 5158 serves to direct light orthogonally from the horizontal input and down into the tube wall, also causing the light to spread around the circumference of the tube wall by the time the light reaches the distal or lower part of the tube. Reflector surfaces such as surface 5158 may be a flat surface, an arced surface, or a series of interconnected surfaces and may also end at the top of the tube wall. Reflector surface 5158 may be treated, e.g., a reflective or metalized coating or an applied reflective film, to enhance reflection.

Air gaps may be used to isolate the light-conducting pathway in any suitable connector. Waveguide 5150 of FIG. 32 includes male connector 5148C that has been integrated with waveguide tube wall 5157 via bracket 5147. This allows connector 5148C to be molded with the waveguide and not attached as a separate part, such as standard light connector 5152C shown in FIG. 28. A separate connector introduces tolerance concerns into the system that may result in reduced coupling efficiency between a fiber optic cable output and waveguide input 5149 because the two parts may not be aligned correctly. Molding the connector and the waveguide input as one piece substantially reduces the chance of misalignment and thereby increases coupling efficiency. Optical cladding may be applied to the surface of any portion of waveguide/cannula 5150 in order to prevent light loss.

Figure 33:
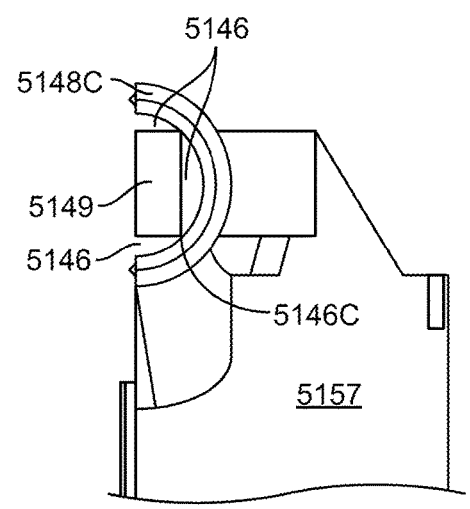
FIG. 33 is close up front view of the input connector of claim 32.

FIG. 33 is a front view looking into the input of connector 5148C. Air gaps 5146 are maintained around waveguide input 5149 to isolate the light-conducting pathway. One or more small zones of contact such as contact zone 5146C may be maintained, essentially bridging connector 5148C and input 5149 with a small amount of material, to add strength and stability to the system while resulting in minimum light loss in the contact zone. Optical cladding may be applied to contact zone 5146C to prevent light loss.

Figure 34:
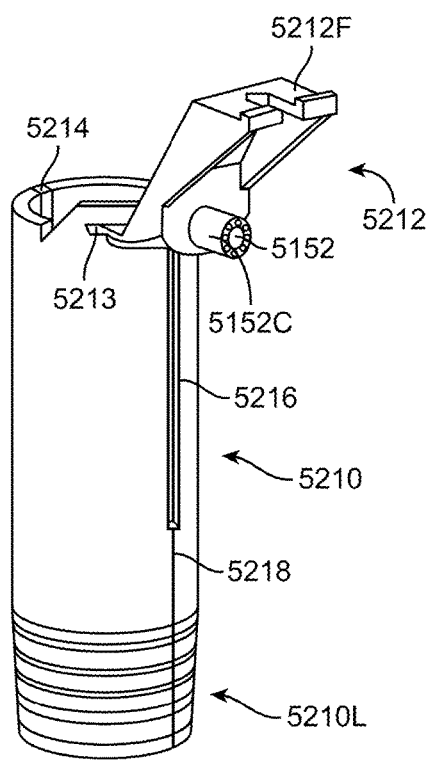
FIG. 34 is a perspective view of a separable waveguide.
Figure 35:
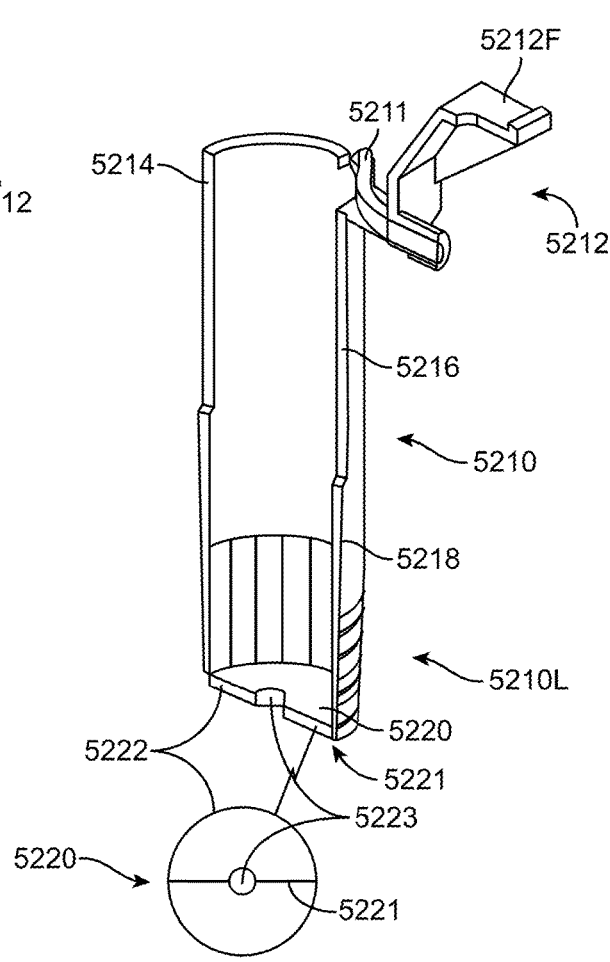
FIG. 35 is a cutaway view of the optical waveguide of FIG. 34.

Waveguide 5210 of FIGS. 34 and 35 may be split open during surgery to permit greater access to the surgical field. Waveguide 5210 may be rigid optical material, e.g., acrylic or polycarbonate, or may be flexible optical material, e.g., silicone, or may incorporate both flexible and rigid elements, e.g. a silicone waveguide hinge over-molded to an upper and lower rigid acrylic waveguide. Light input channels 5211 and 5213 may be split and fed through a fiber "Y" or may be comprised entirely of optical fibers. Fibers may be embedded into the wall of the wave-guide all the way to lower portion 5210L that may incorporate light extraction structures. Waveguide 5210 may be fully split front and back from the top to about ½-⅔ of tube by slots 5214 and 5216. Alternatively, a waveguide may be split all the way to lower portion 5210L. Lower portion 5210L is scored inside and out with scoring such as score 5218. Alternatively, the waveguide 5210 may not be split at all. The scoring operates to redirect light stuck circling the tube. The optional bottom element 5220 may be pre-split in half along edge 5221 and may be glued or otherwise secured in a waveguide such as waveguide 5210. When present, the planar shape of element 5220 permits viewing through bottom element 5220 and allows light to shine through. Alternatively, element 5220 may also adopt any other suitable geometry such as rounded to form a lens. Because of the interface with the tube along edge 5222 very little light is conducted into element 5220. Hole 5223 enables a surgical screw or other suitable connector to engage through the bottom of waveguide 5210 to a surgical site. Splitting waveguide 5210 and bottom 5220 frees the waveguide elements from the connector, and permits the waveguide elements to be removed from the surgical site. While at least one light extraction structure is preferably located in lower portion 5210L on each tube half, the at least one extraction structure may be located on only one half or may be located further up the tube, e.g., near the end of split 5216 and or split 5214. At least a portion of waveguide 5210 may feature cladding layer 5199 to enhance TIR. Cladding layer 5199 may be disposed on at least a part of the internal or external wall surface of waveguide 5210.

Figure 36:
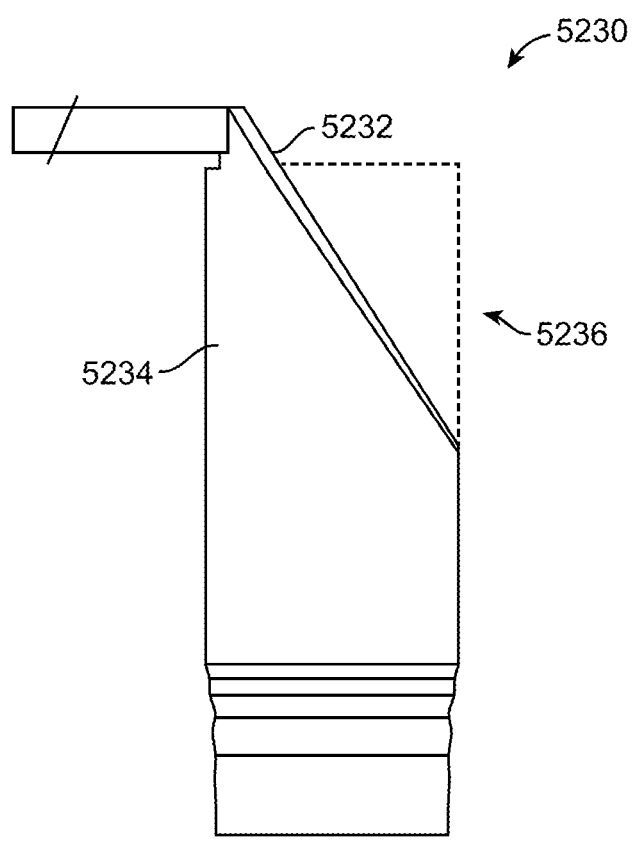
FIG. 36 is a cutaway view of an optical waveguide with an extended reflecting surface.

Waveguide 5230 in FIG. 36 has reflector face 5232 extending down to the opposite side of tube waveguide 5234, effectively removing material 5236. Extended reflector face 5232 serves to direct light circumferentially around the tube wall. This opens up the waveguide to provide improved access to the surgical space. In addition, it offers the opportunity to replace removed material 5236 with more durable material to improve strength and or provide the clamp flange holder function and or to provide mounting for other devices, such as a CCD camera. Cladding layer 5199 may be disposed on at least a part of the internal or external wall surface of waveguide 5230.

Illuminated retractors such as cannula, waveguides, tubes and or sheaths may also benefit from extendable skirts or segments to prevent tissue encroaching on a surgical site. The extendable elements may also include interface surfaces to introduce light into the elements to enhance surgical site illumination and or provide off axis illumination to enhance shadows for better depth perception and tissue discrimination.

The illuminated retractors as discussed above may also be made extendable or telescoping to enable use in varying depths of surgery with a single device thereby minimizing hospital inventory. The illuminating cannulas discussed may also be formed as an illuminating drill guide, either as a tube or as two half tubes, that may be used to hold and guide drill or burr tip while also providing illumination of the area being worked on.

Figure 37:
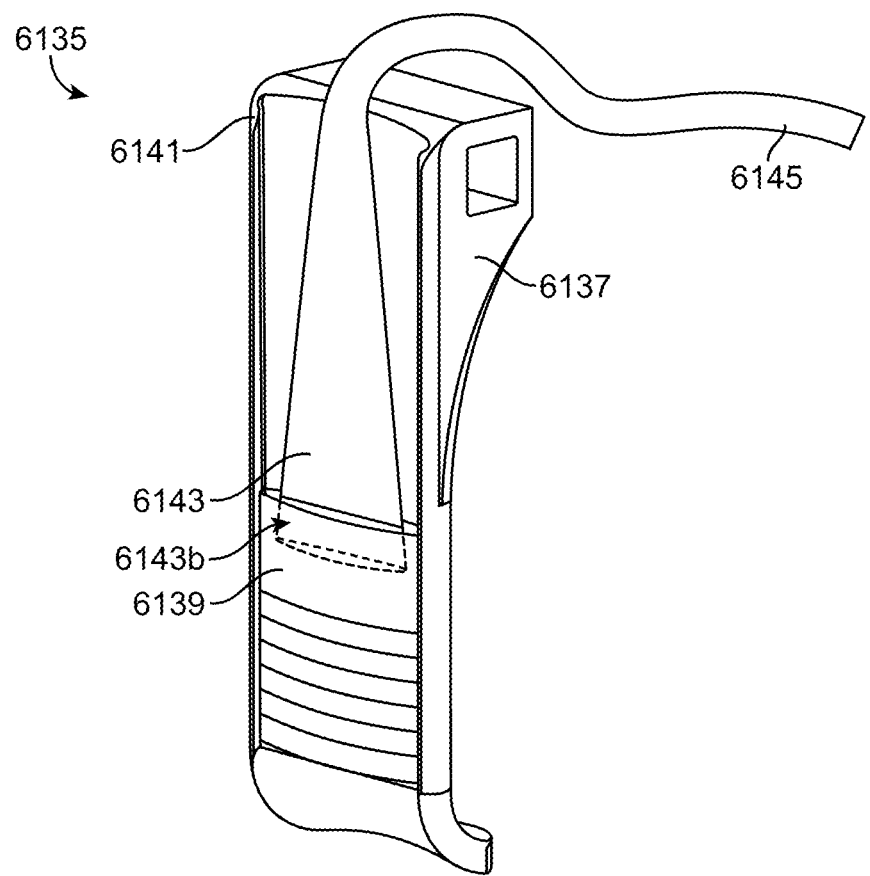
FIG. 37 illustrates a pigtail connection to a non-fiber optical waveguide.

FIG. 37 shows a pigtail connection to a non-fiber optical waveguide. FIG. 37 depicts a retractor illumination system 6135 comprised of retractor 6137 configured to allow waveguide (also referred to as light guide) 6139 to slide into grooves 6141 formed into retractor 6137. Alternatively, light guide 139 may be configured to slide around the sides of retractor 6137 or snap onto or into retractor 6137. The waveguide may alternatively be a part of any waveguide/surgical instrument described in this application and is not limited to retractors. Light guide 6139 has flexible input 6143 that is attached to light guide using a suitable method, such as insert molding, co-molding or via adhesive, preferably an index matching adhesive to minimize light loss at it transfers from flexible input 6143 into light guide 6139. Flexible input 6143 may be formed from a suitable, flexible, light conducting material such as one or more fiber optic cables or silicone. Flexible input 6143 may be flared into light guide 139 to help start distributing light across the width of light guide 6139 and to match the thin profile of light guide 139 inside of the surgical work space. Proximal end 6145 of flexible input 6143 may be a short length of flexible material with a suitable optical connector that is connected via a separate fiber optic cable to a light source, or it may be of a longer length to form a cable that connects directly to a suitable light source. Flexible portion 6143 may abut light guide 6145 or alternatively comprise a portion 6143b adapted to protrude into light guide 6145 in order to facilitate optical coupling therebetween. This embodiment suffers in that flexible input 6143 lies over the top of retractor 6137 and may be subject to damage from instruments used during surgery. Alternatively, flexible input 6143 may be positioned underneath frame bar and thereby protecting flexible input 6143.

Figure 38:
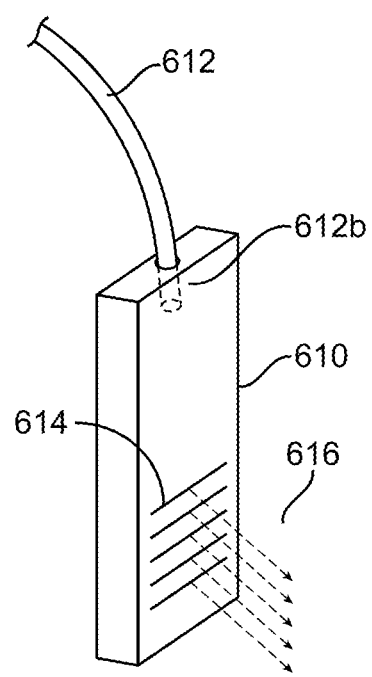
FIGS. 38 and 39 show illustrate optical connections for non-fiber optical waveguides

FIG. 38 shows an alternative optical connection for a non-fiber optical waveguide. Flexible fiber optic 612 which may be optically coupled to an external light source (not shown) may terminate inside a "receiving portion" of non-fiber optical waveguide 610. Fiber optic 612 may be a single fiber or a bundle of fibers. Fiber optic 612 may abut the receiving portion of waveguide 610. Alternatively, fiber optic 612 may comprise a portion 612b that protrudes into waveguide 610 in order to facilitate optical coupling therebetween. The receiving portion being configured to receive light from the terminus of fiber 612 such that the light is conducted within the waveguide 610 via TIR. Extraction features 614 then extract the conducted light and direct such light 616 to exit the waveguide to thereby illuminate the surgical field.

Figure 39:
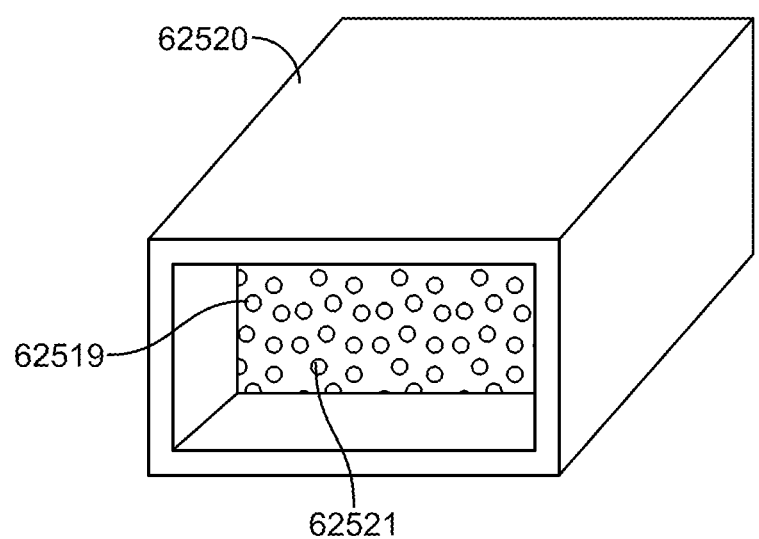

FIG. 39 shows an optional optical coupling for a non-fiber optical waveguide to one or more fiber optical cables which may thereby be coupled to an external light source. Sleeve 62520 contains one or more fiber optic elements 62521 which may be potted in place with epoxy 62519. The sleeve being adapted to fit over a receiving zone of any non-fiber optical waveguide described in this application and to facilitate coupling of light from the fiber optic elements 62521 into the waveguide such that the light is thereby conducted in the waveguide via TIR. The ends of the fibers may be polished and recessed from the end of the sleeve such that they butt against the non-fiber optical waveguide when the sleeve is attached to the waveguide. Index matching adhesive may then be used to attach the optical waveguide to the sleeve and optical fibers.

Figure 40:
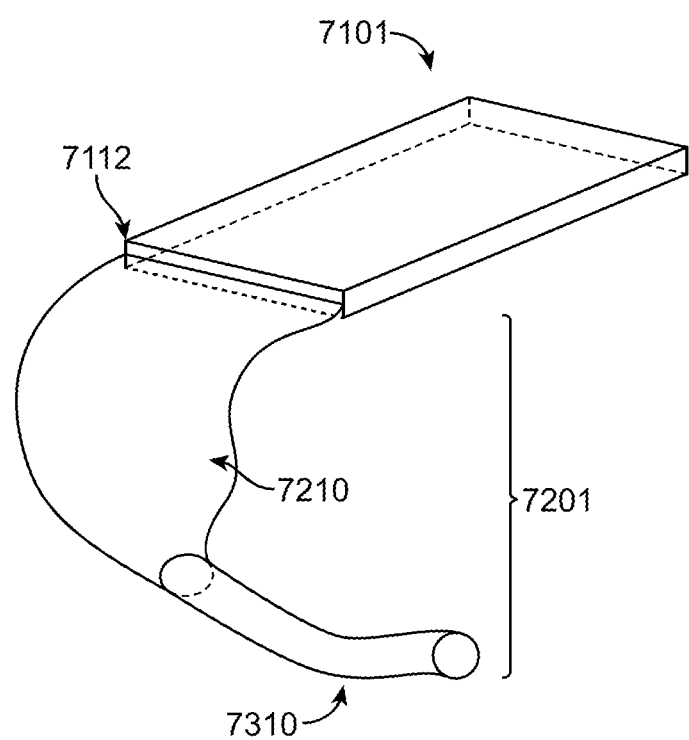
Figure 41A:
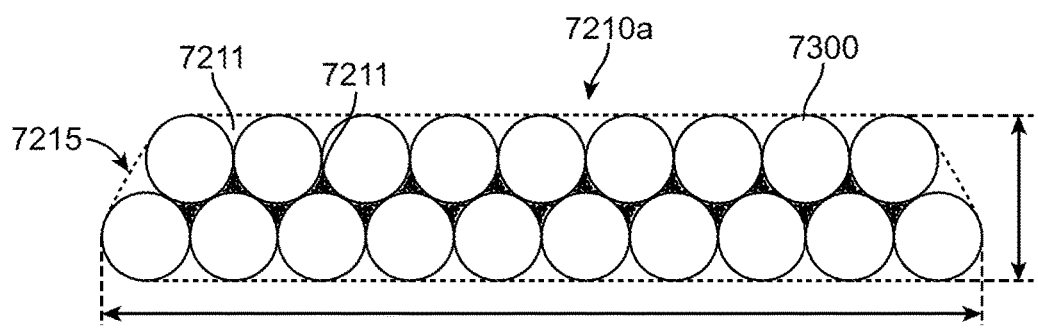
Figure 41B:
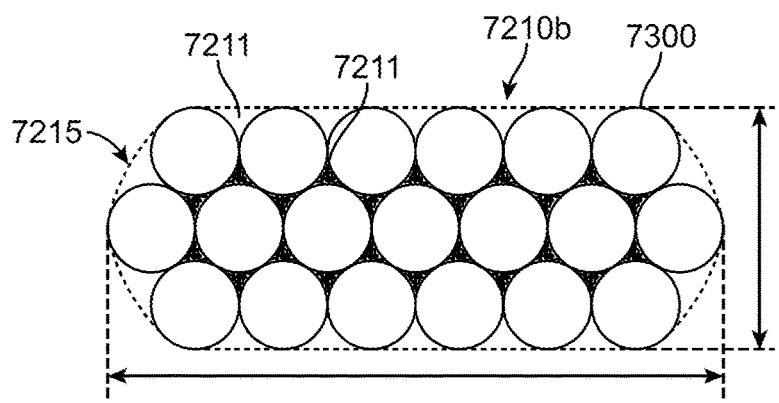

In any of the embodiments described in this application the flexible input may comprise a fiber optic ribbon and/or cable. FIG. 40 shows a fiber optic waveguide 7101 having a receiving portion 7112 that is optically coupled to a flexible input 7201. Waveguide 7101 may be a part of a surgical device such as any of those described herein. As illustrated in FIG. 40, the flexible input comprises a fiber optic ribbon 7201 having a substantially flat flexible portion 7201. This ribbon portion may transition into a cable portion having a substantially cylindrical cross section. Such ribbons are described in detail in U.S. patent application Ser. No. 14/035,583 which is hereby incorporated by reference in its entirety. A section of portion 7210 may comprise a plurality of optical fibers splayed out into one or more rows such that portion 7210 has a width substantially larger than its height. FIG. 41A shows ribbon portion 7210a with an arrangement of 19 optical fibers 7300 arranged in 2 rows. FIG. 41B shows a similar ribbon portion 7210b with an arrangement of the 19 optical fibers 7300 into 3 rows. The ribbon portion is not limited to 2 or 3 row configurations; any appropriate number of rows may be used. Optionally a single row is used. The interstitial spaces 7211 between each optical fiber may comprise optical cladding material and/or other cladding materials. At least a portion of the surface of one or more of the optical fibers 7300 may comprise an optical cladding. Additionally, at least a portion of the exterior surface 7215 of ribbon portion 7210 (7210a and/or 7210b) may be clad with optical cladding material. The flat ribbon portion 7210 is typically flexible and may be bent into a hollow cylinder or another appropriate shape that conforms to the receiving portion 7112 of the waveguide 7101.

The flat ribbon portion 7210 may transition into a cable portion having a substantially round or cylindrical cross section. FIGS. 42A and 42B show two different cable arrangements of the 19 optical fibers 7300. It should be understood that the ribbon/cable arrangement may use any number of optical fibers; 19 are shown here for merely illustrative purposes. Cable arrangement 7310a shows fibers 7300 arranged in concentric hexagons while cable arrangement 7310b shows fibers arranged in concentric circles. These fiber packing arrangements are presented for illustrative purposes and are not limiting; other packing arrangements may be used. Like the flat ribbon section, the interstitial spaces between the fibers may comprise optical cladding material and/or other cladding materials. At least a portion of the surface of one or more of the optical fibers 7300 may comprise an optical cladding. The exterior 7315 of the cable portion 7310 may also comprise optical cladding material.

Many of the disclosed options herein describe an optical cladding applied to the waveguide to help preserve TIR. However, one of skill in the art will appreciate that optionally, instead of applying the cladding to the waveguide, the cladding may be applied to an adjacent surgical instrument to help preserve TIR.

In any of the embodiments disclosed in this specification, any of the coatings or cladding may be used, substituted or combined with one another. Preferred embodiments utilize a fluoro polymer such as Teflon AF7500 because it has desirable optical cladding capability, although it some circumstances adhesion may be challenging. Cytonix Fluoro Acryl 6298 is also a preferred cladding material because it has desirable optical cladding properties and it is similar to FEP shrink wrap which has also been used successfully. MY Polymer 133 may be a useful cladding material, as well as Ovation Opti Clad 134 which may no longer be commercially available.

Therefore, amorphous fluoropolymers such as amorphous PTFE are promising because of their optical cladding properties, although some supplies prefer not to provide this material for medical applications. Fluoro Acrylates are also promising cladding material since they have desirable optical cladding properties and in general are easy to apply to an optical waveguide. In certain circumstances Raymat 137 may be used, but it can also be too gummy and also may require a hard overcoating in order to be useful.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A surgical illumination system for illuminating a surgical field comprising:
   an optical fiber; and
   an optical tip having a bore, wherein the optical fiber is disposed in the bore, and wherein the optical tip further comprises an output zone having a plurality of microstructures for directing light away from the optical tip towards the surgical field;
   an optical cladding layer provided on the output zone and comprising a mask pattern, wherein the mask pattern provides one or more uncladded regions within one or more areas covered by the optical cladding layer,
   wherein the plurality of microstructures comprises a plurality of prisms, the plurality of prisms configured to refract light passing therethrough, and wherein at least some of the plurality of prisms remain uncovered by the optical cladding layer.

2. A surgical illumination system for illuminating a surgical field comprising:
   an optical fiber;
   an optical tip having a bore, wherein the optical fiber is disposed in the bore, and wherein the optical tip further comprises an output zone having a plurality of microstructures for directing light away from the optical tip towards the surgical field; and
   a first optical cladding layer formed on the output zone and comprising a mask pattern, wherein the mask pattern provides one or more uncladded regions within one or more areas covered by the optical cladding layer,
   wherein the plurality of microstructures comprises a plurality of prisms, the plurality of prisms configured to refract light passing therethrough, and
   wherein at least a portion of the plurality of prisms remains uncovered by the optical cladding layer.

3. A surgical illumination system for illuminating a surgical field comprising:
   a cannula having a proximal end, a distal end, a bore therebetween that proceeds along a longitudinal axis of the cannula, an inner surface, an outer surface, the cannula being formed of a polymeric material, wherein the bore is sized and dimensioned to accommodate one or more surgical instruments;
   an optical waveguide adapted to conduct light via total internal reflection from the proximal end of the cannula to the distal end of the cannula;
   one or more light extracting structures provided on a light extraction surface of the optical waveguide near the distal end of the cannula configured to extract the conducted light from the optical waveguide and direct said conducted light to the surgical field, wherein at least some of the one or more light extracting structures comprise one or more prisms;
   at least one optical cladding layer disposed at least on the light extraction surface of the optical waveguide, the at least one optical cladding layer comprising a mask pattern, wherein the mask pattern provides one or more uncladded regions within one or more areas covered by the optical cladding layer, wherein the at least one optical cladding layer is configured to prevent or minimize evanescent waves of the conducted light from coupling to a medium adjacent the optical waveguide, and
   wherein at least a portion of the one or more prisms remains uncovered by the at least one optical cladding layer.

4. The surgical illumination system of claim 3, further comprising one or more light conducting conduits integrated into the proximal end of the cannula for introducing light into at least one of the cannula or the optical waveguide.

5. The surgical illumination system of claim 3, wherein a wall of the cannula forms the optical waveguide.

6. The surgical illumination system of claim 3, wherein the optical waveguide comprises a plurality of light directing elements formed into the surface of the cannula for directing light from the proximal end to the distal end of the cannula.

7. The surgical illumination system of claim 6, wherein the light directing elements comprise: one or more prisms formed in the outer surface of the cannula, the prism oriented parallel to the longitudinal axis of the cannula.

8. The surgical illumination system of claim 6, wherein the light directing elements comprise: one or more prisms formed in the outer surface of the cannula, the prism oriented parallel to the longitudinal axis of the cannula.

9. The surgical illumination system of claim 3, wherein the light extracting structures comprise: one or more circumferential facets formed at an obtuse angle to an adjacent distal cannula surface.

10. The surgical illumination system of claim 3, further comprising one or more additional cladding layers, wherein one or more additional cladding layers modifies one or more physical properties of the at least one optical cladding layer, and wherein the one or more physical properties includes one or more of: durability, hardness, surface porosity, reflectance, electrical conductivity, thermal conductivity, an ability to support or hinder microbial growth, one or more magnetic properties, surface texture, and hydrophobicity.

11. A surgical illumination system for illuminating a surgical field comprising:
   a cannula having a proximal end, a distal end, a bore therebetween that proceeds along a longitudinal axis of the cannula, an inner surface, an outer surface, the cannula being formed of a polymeric material, the polymeric material being configured to conduct light via total internal reflection, thereby allowing the cannula to conduct light from the proximal end to the distal end thereby forming an optical waveguide, wherein the bore is sized and dimensioned to accommodate one or more surgical instruments;
   one or more light extracting structures provided on a light extracting surface near the distal end of the cannula configured to extract the conducted light from the cannula to and direct said conducted light to the surgical field, the one or more light extracting structures comprising one or more prisms;
   at least one optical cladding layer disposed on the light extracting surface of the cannula, the at least one optical cladding layer comprising a mask pattern, wherein the mask pattern provides one or more uncladded regions within one or more areas covered by the optical cladding layer, wherein the at least one optical cladding layer is configured to prevent or minimize evanescent waves of the conducted light from coupling to cannula's surroundings, and wherein at least a portion of the one or more prisms remains uncovered by the optical cladding layer.

12. The surgical illumination system of claim 11, further comprising one or more additional cladding layers, wherein one or more additional layers modifies one or more physical properties of the at least one optical cladding layer, and wherein the one or more physical properties includes one or more of: durability, hardness, surface porosity, reflectance, electrical conductivity, thermal conductivity, an ability to support or hinder microbial growth, one or more magnetic properties, surface texture, and hydrophobicity.

13. A surgical illumination system for illuminating a surgical field comprising:
   a surgical instrument;
   a non-fiber optical waveguide engaged with at least a portion of the surgical instrument, the optical waveguide being configured to conduct light to the surgical field, and wherein the optical waveguide comprises a light extraction surface having one or more light extracting structures configured to extract the conducted light from the optical waveguide to the surgical field, the one or more light extracting structures comprising one or more prisms;
   at least one optical cladding layer disposed upon the light extraction surface, the at least one optical cladding layer comprising a mask pattern, wherein the mask pattern provides one or more uncladded regions within one or more areas covered by the optical cladding layer, and
   wherein at least a portion of the one or more prisms remains uncovered by the optical cladding layer.

14. The surgical illumination system of claim 13, wherein the surgical instrument comprises one or more of the following: a surgical retractor, a suction instrument, or a cannula.

15. The surgical illumination system of claim 13, wherein the at least one optical cladding layer comprises a material having an index of refraction greater than 1 and less than an index of refraction of the optical waveguide's light conducting material.

16. The surgical illumination system of claim 13, wherein the at least one optical cladding layer comprises a polytretrafluoroethylene (PTFE).

17. The surgical illumination system of claim 13, wherein the at least one optical cladding layer comprises fluorinated ethylene propylene (FEP).

18. The surgical illumination system of claim 13, wherein the at least one optical cladding layer comprises perfluoroalkoxy (PFA).

19. The surgical illumination system of claim 13, wherein the at least one optical cladding layer comprises ethylene tetrafluoroethylene (ETFE).

20. The surgical illumination system of claim 13, wherein the at least one optical cladding layer comprises plychlorotrifluoroethylene (PCTFE).

21. The surgical illumination system of claim 13, wherein the at least one optical cladding layer comprises polyvinylfluoride (PVF).

22. The surgical illumination system of claim 13, wherein the at least one optical cladding layer comprises polyethylenechlorotrifluoroethylene (ECTFE).

23. The surgical illumination system of claim 13, wherein the at least one optical cladding layer comprises perfluorinated elastomer.

24. The surgical illumination system of claim 13, wherein the at least one optical cladding layer comprises fluorocarbon.

25. The surgical illumination system of claim 13, wherein the at least one optical cladding layer comprises perfluoropolyether (PFPE).

26. The surgical illumination system of claim 13, wherein the at least one optical cladding layer comprises fluoro silicone.

27. The surgical illumination system of claim 13, wherein the at least one optical cladding layer comprises fluoro acrylate.

28. The surgical illumination system of claim 13, wherein the at least one optical cladding layer comprises fluorourethane alkyd.

29. A surgical illumination system, said system comprising:
   a non-fiber optic optical waveguide for illuminating a surgical field, the optical waveguide comprising a light extraction surface including one or more light extracting structures configured to extract light from the optical waveguide and direct the extracting light to the surgical field, the one or more light extracting structures comprising one or more prisms; and
   a surgical instrument coupled to the non-fiber optic optical waveguide, the surgical instrument having an optical cladding disposed over at least a portion thereof, the optical cladding comprising a mask pattern, wherein the mask pattern provides one or more uncladded regions within one or more areas covered by the optical cladding,
   wherein the optical cladding is disposed between the light extraction surface of the waveguide and the surgical instrument and the optical cladding helps preserve total internal reflection in the waveguide, and
   wherein at least a portion of the one or more prisms remains uncovered by the optical cladding.

30. The surgical illumination system of claim 29, wherein the cladding is 350 nanometers or greater in thickness.

31. The surgical illumination system of claim 29, wherein the cladding comprises a fluoro polymer.

* * * * *